US012588899B2

(12) United States Patent
Sasaki et al.

(10) Patent No.: US 12,588,899 B2
(45) Date of Patent: Mar. 31, 2026

(54) ULTRASONIC DIAGNOSTIC APPARATUS, LEARNING APPARATUS, AND IMAGE PROCESSING METHOD

(71) Applicant: CANON KABUSHIKI KAISHA, Tokyo (JP)

(72) Inventors: Shoya Sasaki, Kanagawa (JP); Naoya Iizuka, Kanagawa (JP); Kenichi Nagae, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/666,676

(22) Filed: May 16, 2024

(65) Prior Publication Data

US 2024/0299011 A1     Sep. 12, 2024

Related U.S. Application Data

(63) Continuation of application No. 17/150,923, filed on Jan. 15, 2021, now Pat. No. 12,016,729.

(30) Foreign Application Priority Data

Jan. 24, 2020    (JP) ................................. 2020-009885
Jan. 24, 2020    (JP) ................................. 2020-010114

(51) Int. Cl.
   *A61B 8/00*         (2006.01)
   *G06N 3/08*         (2023.01)
(52) U.S. Cl.
   CPC .......... *A61B 8/5246* (2013.01); *A61B 8/4444* (2013.01); *A61B 8/461* (2013.01); *G06N 3/08* (2013.01)
(58) Field of Classification Search
   CPC ...... A61B 8/5246; A61B 8/4444; A61B 8/461
   See application file for complete search history.

(56) References Cited

U.S. PATENT DOCUMENTS 5,517,996 A * 5/1996 Okada ................. G01S 7/52019
                                                   600/447
10,335,119 B2  7/2019 Taniguchi
                        (Continued)

FOREIGN PATENT DOCUMENTS

JP        2002301068 A     10/2002
JP        2018023619 A      2/2018
                        (Continued)

OTHER PUBLICATIONS

Simson Walter, et al.; Deep Learning Beamforming for Sub-Sampled Ultrasound Data, 2018 IEEE International Ultrasonics Symposium (IUS), IEEE, Oct. 2018, XP033479985.
                        (Continued)

*Primary Examiner* — Rochelle D Turchen
(74) *Attorney, Agent, or Firm* — Canon U.S.A., Inc. IP Division

(57)          ABSTRACT

An ultrasonic diagnostic apparatus, comprising: an ultrasonic probe which scans an observation region in an object with an ultrasonic wave; and an estimated image generating unit which, by using a model having been machine-learned using learning data including first data based on a first received signal that is obtained by first transmission/reception of an ultrasonic wave and second data based on a second received signal that is obtained by second transmission/reception that represents a larger number of transmissions/receptions than the first transmission/reception of the ultrasonic wave, generates an estimated image equivalent to image data obtained by the second transmission/reception from third data based on a third received signal that is obtained by transmission/reception equivalent to the first transmission/reception of the ultrasonic wave by the ultrasonic probe.

9 Claims, 18 Drawing Sheets

(56)     References Cited

U.S. PATENT DOCUMENTS

| | | | |
|---|---|---|---|
| 2016/0143617 A1 | 5/2016 | Ebbini et al. | |
| 2016/0270763 A1 | 9/2016 | Hayes et al. | |
| 2016/0338670 A1 | 11/2016 | Taniguchi | |
| 2017/0124426 A1 | 5/2017 | Li et al. | |
| 2019/0183462 A1 | 6/2019 | Yang et al. | |
| 2020/0060652 A1 | 2/2020 | Dahl et al. | |
| 2020/0281570 A1 | 9/2020 | Sato et al. | |
| 2020/0320750 A1* | 10/2020 | Yamanaka | G01S 7/5205 |
| 2021/0307726 A1* | 10/2021 | Wernick | A61B 8/54 |

FOREIGN PATENT DOCUMENTS

| | | |
|---|---|---|
| JP | 2019025044 A | 2/2019 |
| JP | 2020179029 A | 11/2020 |
| WO | 2019166332 A1 | 9/2019 |

OTHER PUBLICATIONS

Zixia Zhou et al., High Spatial-Temporal Resolution Reconstruction of Plane-Wave Ultrasound Images With a Multichannel Multiscale Convolutional Neural Network, IEEE Transactions On Ultrasonics, Ferroelectrics, and Frequency Control, Nov. 2018, pp. 1983-1996, vol. 65, No. 11.

* cited by examiner

FIG. 5

| LEARNING DATA ID | INPUT DATA | GROUND TRUTH DATA |
| :---: | :---: | :---: |
| | NORMAL B-MODE IMAGE | SPATIAL COMPOUND IMAGE |
| 1 | B1-1 | SC1-1 (COMPOUND 3, -10°,0°,10°) |
| 2 | B1-1 | SC1-2 (COMPOUND 5, -15°,-10°,0°,10°,15°) |
| 3 | B2-1 | SC2-1 (COMPOUND 5, -15°,-10°,0°,10°,15°) |

FIG. 6

| LEARNING DATA ID | INPUT DATA<br>NORMAL B-MODE IMAGE | GROUND TRUTH DATA<br>FREQUENCY COMPOUND IMAGE |
|---|---|---|
| 4 | B1-1 | FC1-1<br>(COMPOUND 3,<br>2MHz,8MHz) |
| 5 | B1-1 | FC1-2<br>(COMPOUND 4,<br>2MHz,4MHz, 6MHz,8MHz) |
| 6 | B2-1 | FC2-1<br>(COMPOUND 4,<br>2MHz,4MHz, 6MHz,8MHz) |

FIG. 9

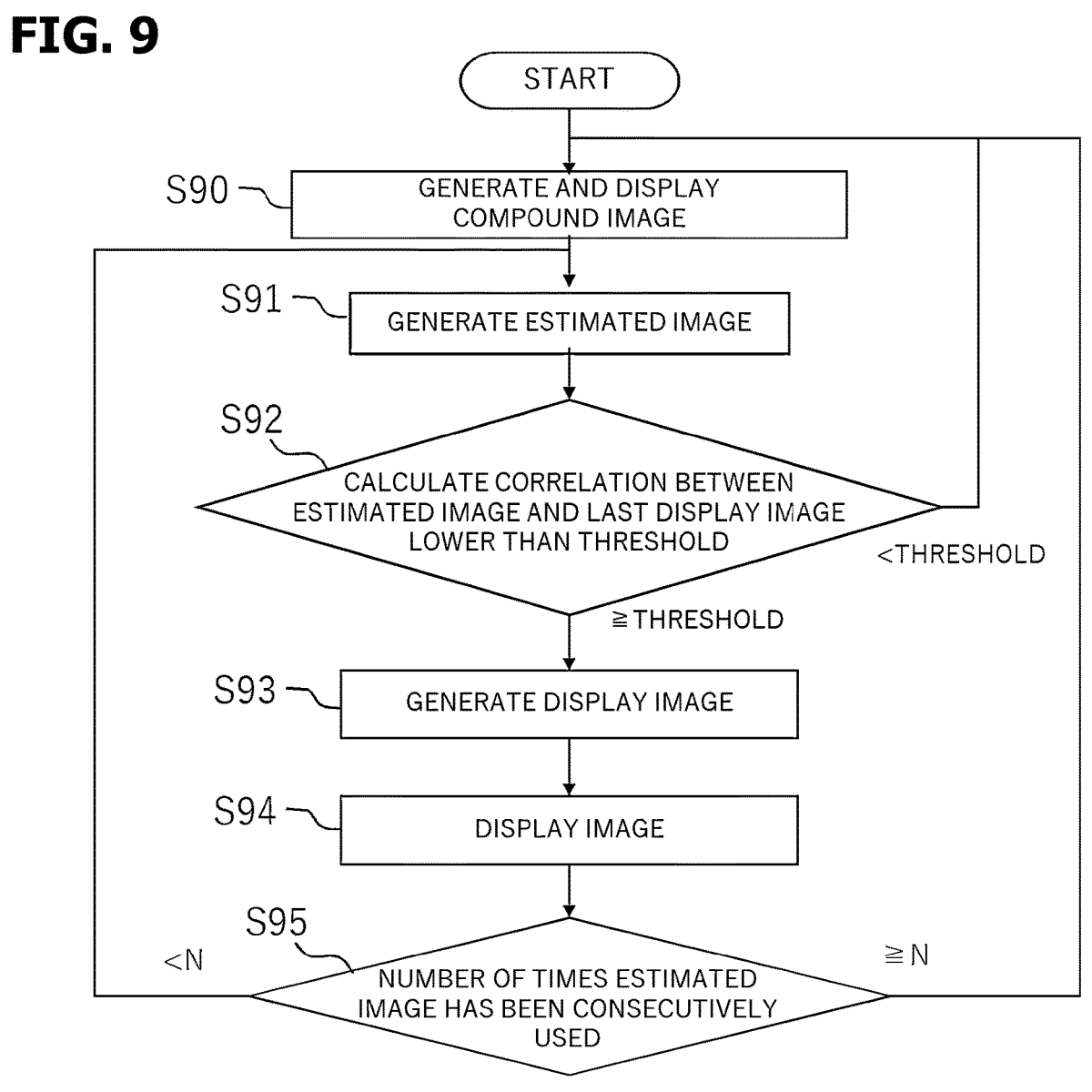

START

S90 — GENERATE AND DISPLAY COMPOUND IMAGE

S91 — GENERATE ESTIMATED IMAGE

S92 — CALCULATE CORRELATION BETWEEN ESTIMATED IMAGE AND LAST DISPLAY IMAGE LOWER THAN THRESHOLD

<THRESHOLD $\geqq$ THRESHOLD

S93 — GENERATE DISPLAY IMAGE

S94 — DISPLAY IMAGE

S95 — NUMBER OF TIMES ESTIMATED IMAGE HAS BEEN CONSECUTIVELY USED

<N $\geqq$ N

COMPOUND MODE    FR:35

NORMAL COMPOUND : ON

AI COMPOUND OFF

COMPOUND MODE    FR:60

NORMAL COMPOUND : ON

AI COMPOUND ON

COMPOUND MODE

NORMAL COMPOUND    FR:35

AI COMPOUND    FR:80

| LEARNING DATA ID | INPUT DATA | | GROUND TRUTH DATA |
| --- | --- | --- | --- |
| | FUNDAMENTAL WAVE IMAGE | TRANSMISSION WAVEFORM MODE | THI IMAGE |
| 1 | B1-1 | THI POSITIVE PULSE | THI1 |
| 2 | B1-2 | THI NEGATIVE PULSE | THI1 |
| 3 | B2-1 | THI POSITIVE PULSE | THI2 |
| 4 | B2-2 | THI NEGATIVE PULSE | THI2 |

1

ULTRASONIC DIAGNOSTIC APPARATUS, LEARNING APPARATUS, AND IMAGE PROCESSING METHOD

CROSS REFERENCE OF RELATED APPLICATIONS

This application is a continuation of U.S. patent application Ser. No. 17/150,923, filed Jan. 15, 2021 which claims the benefit of Japanese Patent Application No. 2020-009885, filed Jan. 24, 2020, and Japanese Patent Application No. 2020-010114, filed on Jan. 24, 2020, all of which are hereby incorporated by reference herein in their entirety.

BACKGROUND OF THE INVENTION

Field of the Invention

The present invention relates to an ultrasonic diagnostic apparatus, a learning apparatus, and an image processing method and, in particular, to a technique for improving image quality of an ultrasonic diagnostic apparatus.

Description of the Related Art

Ultrasonic diagnostic apparatuses are widely used in clinical practice as image diagnostic apparatuses due to, for example, simplicity, high resolution performance, and real-time performance thereof. A general method of generating an ultrasonic image includes beamforming of a transmit beam and phasing addition processing of a received signal. Beamforming of a transmit beam is performed by inputting a voltage waveform provided with a time delay relative to a plurality of conversion elements and causing ultrasonic waves to converge inside a living organism. Phasing addition of a received signal is performed by receiving ultrasonic waves reflected by a structure inside a living organism by a plurality of conversion elements, and providing to obtained received signals a time delay in consideration of a path length with respect to a point of interest, and then adding up the received signals. Due to the beamforming of the transmit beam and the phasing addition processing, reflected signals from the point of interest are selectively extracted to perform imaging. By performing control so that the inside of an imaging region is scanned by the transmit beam, it is possible to obtain an image of a region desired to be observed.

In such ultrasonic diagnostic apparatuses, noise (speckle noise) may be created by random interference of reflected ultrasonic waves from a plurality of reflectors inside an object, whereby image quality of an ultrasonic image may decline. Methods of reducing such noise include compound processing. Further, the compound processing includes spatial compound processing and frequency compound processing. The spatial compound processing refers to a technique of performing transmission/reception of ultrasonic pulses on a same location of an object from a plurality of different directions and combining a plurality of pieces of obtained signal data to create an ultrasonic image. The frequency compound processing refers to a technique of performing transmission/reception of ultrasonic pulses with a plurality of different frequencies on a same location of an object and combining a plurality of pieces of obtained signal data to create an ultrasonic image.

In addition, in such ultrasonic diagnostic apparatuses, imaging (harmonic imaging) of a harmonic component with respect to a fundamental wave component of a transmission signal is widely performed. A method of imaging a harmonic component that is created during a process of an ultrasonic wave propagating inside an object is called tissue harmonic imaging (THI). The tissue harmonic imaging involves extracting a harmonic component caused by unique nonlinearity of an object (body tissue) from a received signal and imaging the inside of the object. The use of a harmonic component created by a non-linear effect improves resolution and reduces artifacts. One method of extracting a harmonic component in tissue harmonic imaging is called a pulse inversion method. In the pulse inversion method, by adding up received signals obtained by transmitting/receiving a first transmission waveform and a second transmission waveform created by inverting a phase of the first transmission waveform, a fundamental wave component is canceled and a harmonic component is enhanced.

Japanese Patent Application Laid-open No. 2018-23619 discloses improving image quality of an ultrasonic image by compound processing. Japanese Patent Application Laid-open No. 2002-301068 discloses a pulse inversion method that improves penetration while maintaining resolution by using a differential sound component in addition to a harmonic component. Japanese Patent Application Laid-open No. 2019-25044 discloses a medical imaging apparatus using a restorer constituted by a neural network.

SUMMARY OF THE INVENTION

Performing the compound processing requires performing transmission/reception of an ultrasonic pulse a plurality of times on a same location of an object. Therefore, there is a problem in that a frame rate declines (simply put, compared to when an image is generated by one transmission/reception, performing N-number of transmissions/receptions causes the frame rate to drop to 1/N). There is another problem in that, when an object or an ultrasonic probe moves while performing the N-number of transmissions/receptions, image quality such as resolution and contrast declines.

In addition, performing tissue harmonic imaging by the pulse inversion method requires performing transmitting/receiving of an ultrasonic pulse a plurality of times on a same location of an object. Therefore, there is a problem in that a frame rate declines (simply put, compared to when an image is generated by one transmission/reception, performing N-number of transmissions/receptions causes the frame rate to drop to 1/N). There is another problem in that, when an object or an ultrasonic probe moves while performing the N-number of transmissions/receptions, image quality such as resolution and contrast declines.

The present invention has been made in consideration of the problems described above and an object thereof is to provide an ultrasonic diagnostic apparatus that enables an image with favorable image quality to be obtained while reducing an effect of a decline in a frame rate.

The present disclosure includes an ultrasonic diagnostic apparatus, comprising: an ultrasonic probe which scans an observation region in an object with an ultrasonic wave; and an estimated image generating unit which, by using a model having been machine-learned using learning data including first data based on a first received signal that is obtained by first transmission/reception of an ultrasonic wave and second data based on a second received signal that is obtained by second transmission/reception that represents a larger number of transmissions/receptions than the first transmission/reception of the ultrasonic wave, generates an estimated image equivalent to image data obtained by the second transmission/reception from third data based on a third received signal that is obtained by transmission/reception equivalent to the first transmission/reception of the ultrasonic wave by the ultrasonic probe.

The present disclosure further includes a learning apparatus comprising a learning unit which performs machine learning of a model using learning data that includes first data based on a first received signal that is obtained by first transmission/reception of an ultrasonic wave and second data based on a second received signal that is obtained by second transmission/reception that represents a larger number of transmissions/receptions than the first transmission/reception of the ultrasonic wave.

The present disclosure still further includes an image processing method comprising a step of, by using a model having been machine-learned using learning data including first data based on a first received signal that is obtained by first transmission/reception of an ultrasonic wave by an ultrasonic probe and second data based on a second received signal that is obtained by second transmission/reception that represents a larger number of transmissions/receptions than the first transmission/reception of the ultrasonic wave, generating an estimated image equivalent to image data obtained by the second transmission/reception of the ultrasonic wave from third data based on a third received signal that is obtained by the first transmission/reception of the ultrasonic wave by the ultrasonic probe.

According to the present disclosure, provided is an ultrasonic diagnostic apparatus that enables an image with favorable image quality to be obtained while reducing an effect of a decline in a frame rate.

Further features of the present invention will become apparent from the following description of exemplary embodiments with reference to the attached drawings.

BRIEF DESCRIPTION OF THE DRAWINGS

FIG. 5 is a diagram showing an example of learning data using a spatial compound image;

FIG. 6 is a diagram showing an example of learning data using a frequency compound image;

FIG. 9 is a diagram representing a flow of processing according to the first embodiment;

FIG. 12 is a block diagram showing details of a received signal processing block according to a second embodiment;

FIG. 16 is a diagram for explaining learning data;

DESCRIPTION OF THE EMBODIMENTS

First Embodiment

Configuration of Ultrasonic Diagnostic Apparatus

Figure 1:
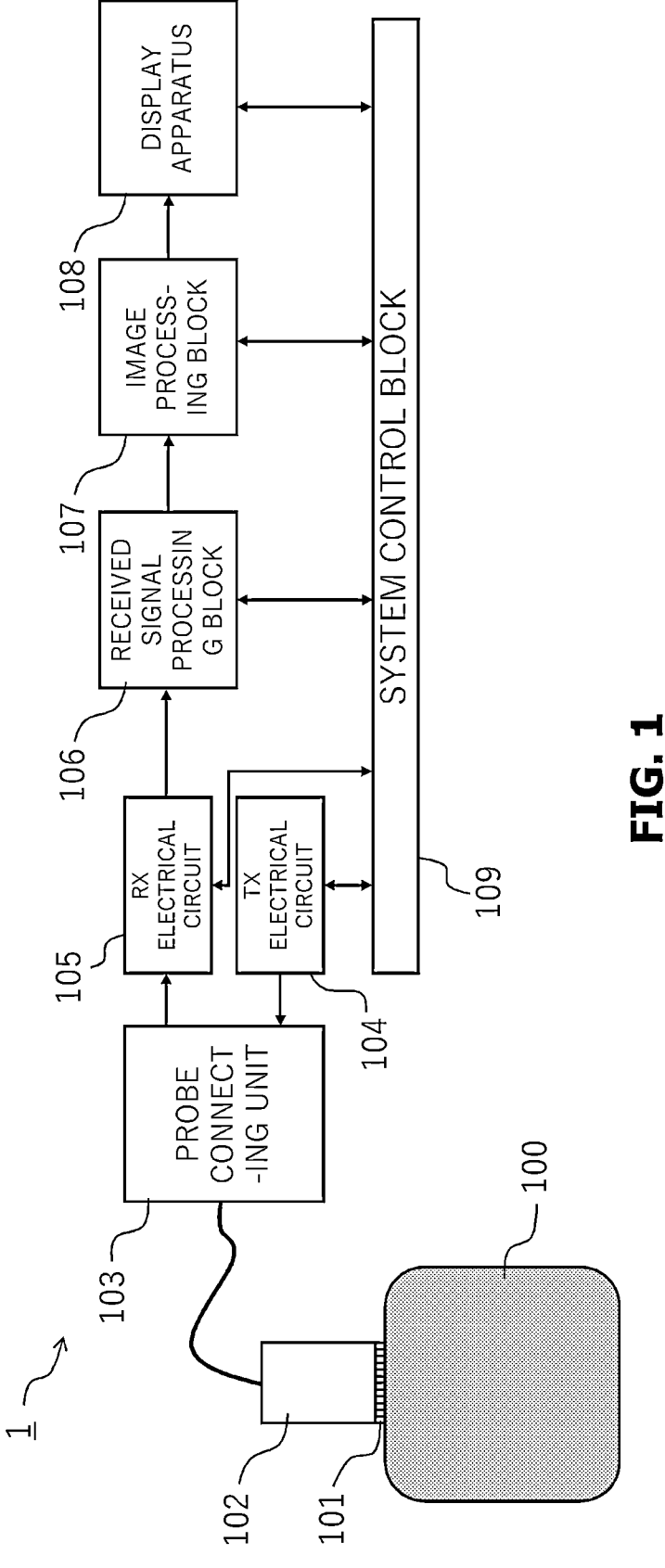
FIG. 1 is a block diagram showing an example of a hardware configuration of an ultrasonic diagnostic apparatus.

A first embodiment of the present invention will be described. FIG. 1 is a block diagram showing an example of a hardware configuration of an ultrasonic diagnostic apparatus. In general, an ultrasonic diagnostic apparatus 1 has an ultrasonic probe (an ultrasonic transducer) 102, a probe connecting portion 103, a transmission electrical circuit 104, a reception electrical circuit 105, a received signal processing block 106, an image processing block 107, a display apparatus 108, and a system control block 109. The ultrasonic diagnostic apparatus 1 is a system for transmitting an ultrasonic pulse to an object 100 from the ultrasonic probe 102, receiving reflected ultrasonic waves having been reflected inside the object 100, and generating image information (an ultrasonic image) of the inside of the object 100. The ultrasonic image obtained by the ultrasonic diagnostic apparatus 1 is to be used in various clinical examinations.

The ultrasonic probe 102 is a probe adopting an electronic scan system and has a plurality of transducers 101 arranged one-dimensionally or two-dimensionally at a tip thereof. The transducer 101 is an electric mechanical conversion element that performs mutual conversion between an electric signal (a voltage pulse signal) and an ultrasonic wave (an acoustic wave). The ultrasonic probe 102 transmits ultrasonic waves from the plurality of transducers 101 to the object 100 and receives reflected ultrasonic waves reflecting a difference in acoustic impedances inside the object 100 by the plurality of transducers 101.

The transmission electrical circuit 104 is a transmitting unit that outputs a pulse signal (a drive signal) with respect to the plurality of transducers 101. By applying a pulse signal with a time difference with respect to the plurality of transducers 101, ultrasonic waves with different delay times are transmitted from the plurality of transducers 101 and a transmission ultrasonic beam is formed. By selectively changing the transducer 101 to which the pulse signal is applied (in other words, the transducer 101 to be driven) and changing a delay time (an application timing) of the pulse signal, a direction and a focus of the transmission ultrasonic beam can be controlled. An observation region inside the object 100 is scanned by sequentially changing the direction and the focus of the transmission ultrasonic beam. The reception electrical circuit 105 is a receiving unit that inputs, as a received signal, an electric signal output from the transducer 101 having received a reflected ultrasonic wave. The received signal is input to the received signal processing block 106. Operations of the transmission electrical circuit 104 and the reception electrical circuit 105 or, in other words, transmission/reception of ultrasonic waves is controlled by the system control block 109. It should be noted that, in the present specification, both an analog signal output from the transducers 101 and digital data obtained by sampling (digitally converting) the analog signal will be referred to as a received signal without particular distinction. However, a received signal may sometimes be described as received data depending on the context in order to clearly indicate that the received signal is digital data.

The received signal processing block 106 generates image data based on a received signal obtained from the reception electrical circuit 105. The image processing block 107 applies image processing such as brightness adjustment, interpolation, and filter processing on the image data generated by the received signal processing block 106. The display apparatus 108 is a display unit for displaying image data and various kinds of information and is constituted by, for example, a liquid crystal display or an organic EL display. The system control block 109 is a control unit that integrally controls the transmission electrical circuit 104, the reception electrical circuit 105, the received signal processing block 106, the image processing block 107, the display apparatus 108, and the like.

Configuration of Received Signal Processing Block

Figure 2:
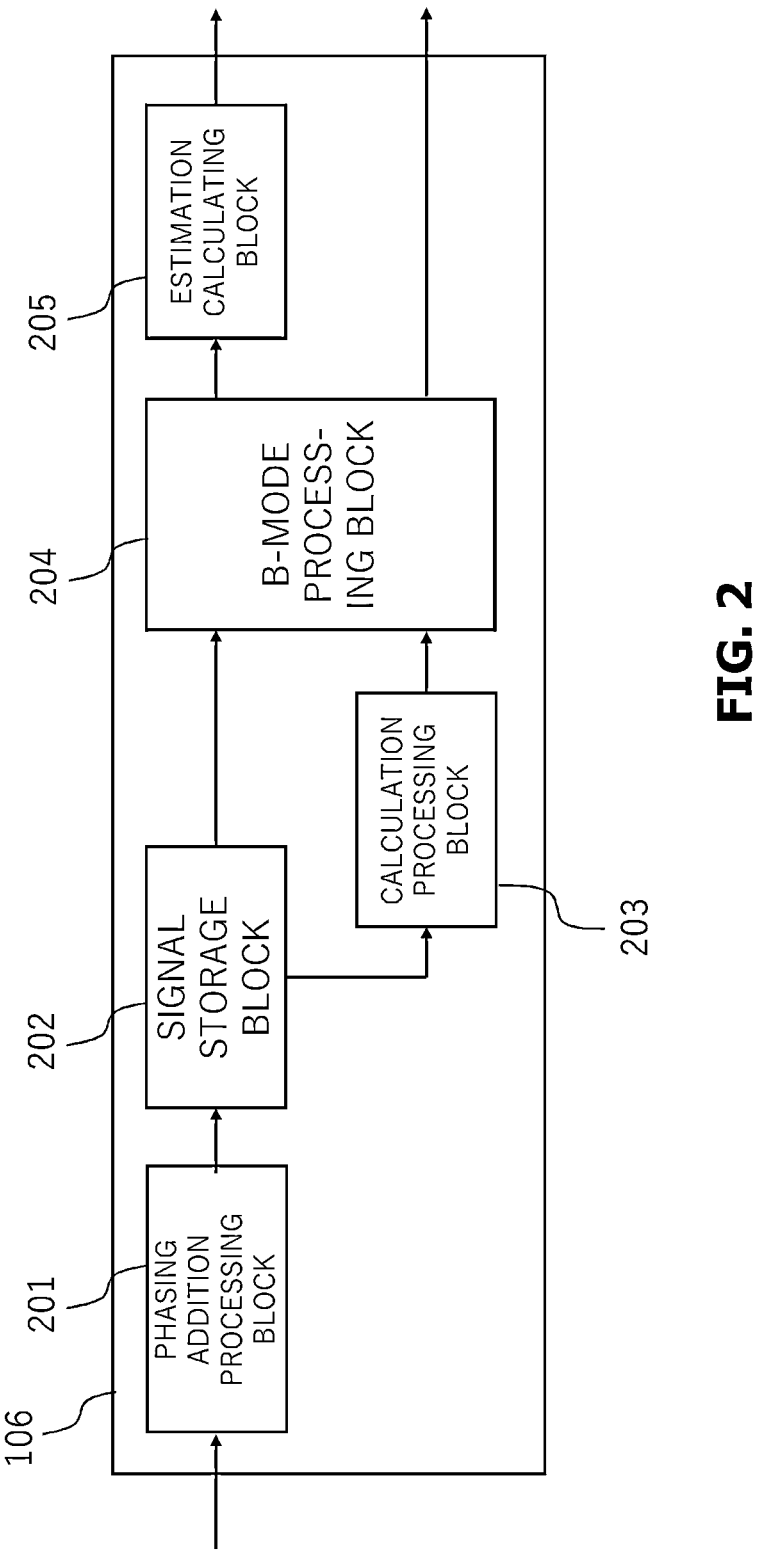
FIG. 2 is a block diagram showing details of a received signal processing block according to a first embodiment.

FIG. 2 is a block diagram showing an example of functions included in the received signal processing block 106. The received signal processing block 106 has a phasing addition processing block 201, a signal storage block 202, a calculation processing block 203, a B-mode processing block 204, and an estimation calculating block 205. In the present embodiment, the calculation processing block 203, the B-mode processing block 204, and the estimation calculating block 205 respectively correspond to the "combining unit", the "image generating unit", and the "estimated image generating unit" according to the present invention.

The phasing addition processing block 201 performs phasing addition on received signals obtained from the reception electrical circuit 105 and saves the added received signal in the signal storage block 202. Phasing addition processing refers to processing for forming a received ultrasonic beam by varying a delay time for each transducer 101 and adding up received signals of the plurality of transducers 101 and is also called Delay and Sum (DAS) beamforming. The phasing addition processing is performed by the phasing addition processing block based on an element arrangement and various conditions of image generation (aperture control and signal filtering) that are supplied from the system control block 109.

The calculation processing block 203 generates an ultrasonic signal after compound processing according to a method to be described later. The received signal saved in the signal storage block 202 and the ultrasonic signal after the compound processing are transmitted to the B-mode processing block 204. The B-mode processing block 204 performs envelope detection processing, logarithmic compression processing, and the like and generates image data in which signal strength at each point inside the observation region is expressed by brightness intensity. Using a model having been machine-learned using learning data including first data based on a first received signal obtained by one scan of an ultrasonic wave and second data based on a second received signal obtained by a plurality of scans in which a transmission direction or a central frequency of the ultrasonic wave has been changed, the estimation calculating block 205 (the estimated image generating unit) generates an estimated image corresponding to image data obtained by a plurality of scans in which a transmission direction or a central frequency of the ultrasonic wave has been changed from third data based on a third received signal obtained by one scan of an ultrasonic wave by the ultrasonic probe 102 (the ultrasonic transducer). In the present specification, an "estimated image corresponding to image data obtained by a plurality of scans in which a transmission direction or a central frequency of the ultrasonic wave has been changed" is also referred to as a "compound processing-equivalent image". A compound processing-equivalent image can also be considered an image subjected to image quality improvement that is equivalent to an image (referred to as a compound image) generated using an ultrasonic signal after compound processing by applying image processing (estimation calculation processing) on one ultrasonic image. Generation of a compound processing-equivalent image by the estimation calculating block 205 can also be referred to as pseudo-compound processing or AI (artificial intelligence) compound processing, and a compound processing-equivalent image can also be referred to as a pseudo-compound image or an AI compound image. In accordance with control of the system control block 109, the received signal processing block 106 is capable of switching among images to be generated and output by the received signal processing block 106. For example, the system control block 109 can select an image to be output from a normal B-mode image, a compound image, and a compound processing-equivalent image. The image to be output from the received signal processing block 106 is subjected to prescribed processing by the image processing block 107 and subsequently displayed by the display apparatus 108.

The received signal processing block 106 may be constituted by at least one processor and a memory. In this case, functions of the respective blocks 201 to 205 shown in FIG. 2 are to be realized by a computer program. For example, the functions of the respective blocks 201 to 205 can be provided by having a CPU load and execute a program stored in the memory. Other than the CPU, the received signal processing block 106 may include a processor (a GPU, an FPGA, or the like) responsible for operations of the calculation processing block 203 and operations of the estimation calculating block 205. In particular, an FPGA is effectively used in the calculation processing block 203 to which a large amount of data is input at the same time and a GPU is effectively used when executing operations in an efficient manner as in the estimation calculating block 205. The memory favorably includes a memory for storing a program in a non-transitory manner, a memory for temporarily saving data such as a received signal, and a working memory to be used by the CPU.

Compound Processing

An image generation method according to spatial compound processing and frequency compound processing which constitute compound processing will now be described.

Figure 3:
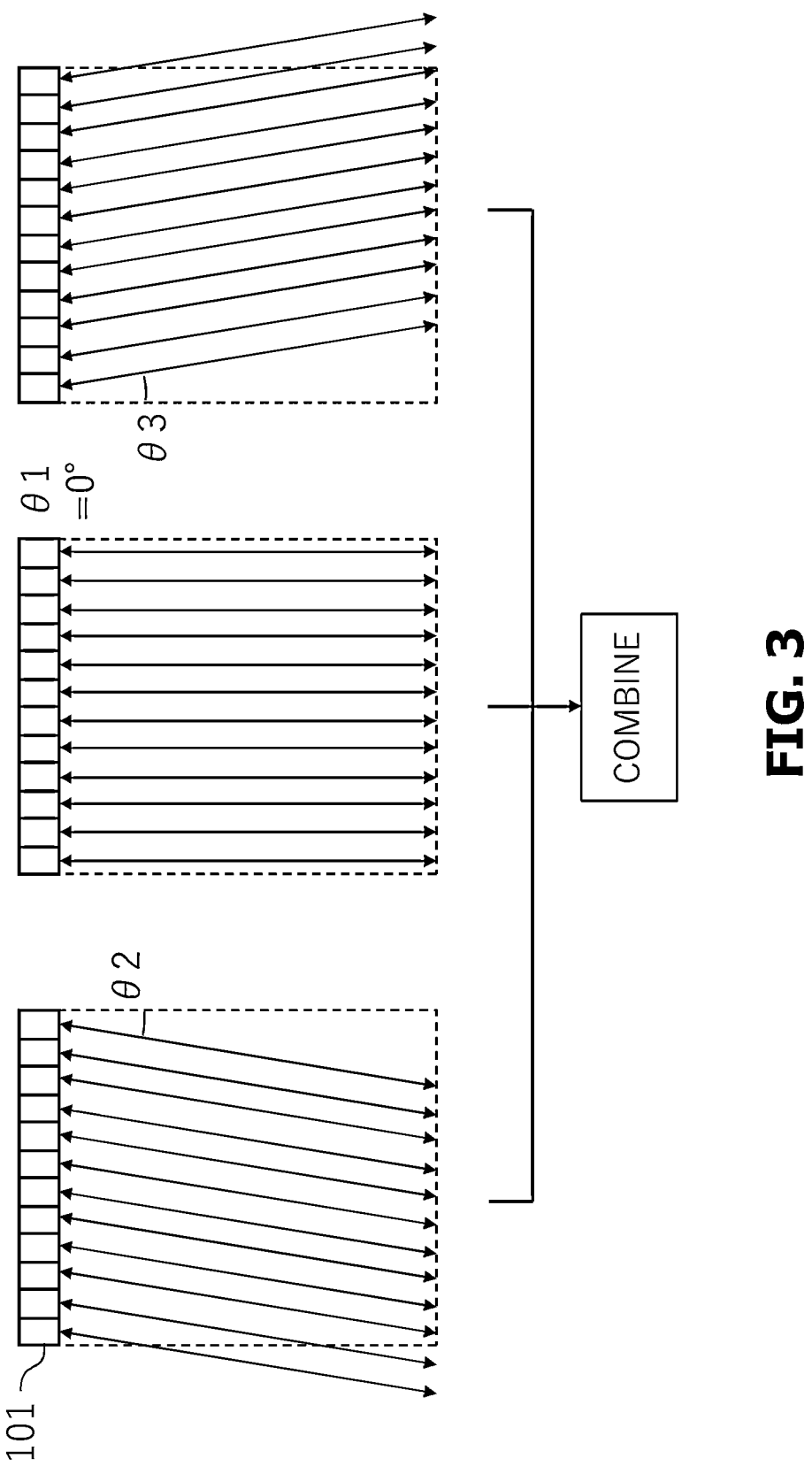
FIG. 3 is a diagram for illustrating spatial compound processing.

Spatial compound processing refers to a technique for performing transmission/reception of an ultrasonic wave with respect to a same location of an object from a plurality of different directions and combining a plurality of pieces of obtained signal data to create an ultrasonic image. Spatial compound processing has an effect of increasing uniformity of an ultrasonic image and improving connection of peripheral echoes in a lesion part or the like. As shown in FIG. 3, by scanning a same location of an object a plurality of times while changing a transmission direction of an ultrasonic beam and acquiring received signals corresponding to the respective transmission directions, a plurality of pieces of frame data representing different transmission directions of the ultrasonic beam are obtained. The pieces of frame data are averaged and combined to generate one frame's worth of frame data, and an ultrasonic image is generated based on the frame data. FIG. 3 shows an example of combining three pieces of frame data obtained by three scans (deflection angle $\theta=\theta 1$, $\theta 2$, $\theta 3$). When combining a plurality of pieces of frame data, weighting addition or the like may be performed besides averaging to generate one frame's worth of frame data from the plurality of pieces of frame data. Since a plurality of pieces of frame data with different patterns of speckle noise or artifacts are obtained by imaging a same location of an object from different directions, an ultrasonic image with reduced speckle noise or artifacts can be obtained by combining the plurality of pieces of frame data.

However, since spatial compound processing requires a plurality of scans (imaging in a plurality of directions) as compared to normal processing in which an ultrasonic image is generated by only one scan (imaging in one direction), the frame rate declines. For example, as shown in FIG. 3, when three scans are performed by changing the deflection angle to $\theta 1$, $\theta 2$, and $\theta 3$, the frame rate drops to ⅓ as compared to normal processing in which an ultrasonic image is generated by only one scan. In addition, when the ultrasonic probe 102 or the object moves while performing the plurality of scans, since a position of the object in each piece of frame data deviates, combining such frame data may result in a decline in image quality such as resolution or contrast.

Frequency compound processing refers to a technique for performing transmission/reception of ultrasonic pulses with a plurality of different central frequencies with respect to a same location of an object and combining a plurality of pieces of obtained signal data to create an ultrasonic image. Frequency compound processing has an effect of improving azimuth resolution and improving image uniformity. For example, an observation region of an object is scanned with an ultrasonic beam with a central frequency of f1 and a received signal corresponding to the ultrasonic beam with the central frequency f1 is acquired. Furthermore, the same observation region is scanned with an ultrasonic beam with a central frequency of f2 ($\neq$f1) and a received signal is acquired. Accordingly, a plurality of pieces of frame data with different central frequencies of an ultrasonic beam are obtained. The pieces of frame data are averaged and combined to generate one frame's worth of frame data, and an ultrasonic image is generated based on the frame data. When combining the plurality of pieces of frame data, weighting addition or the like may be performed besides averaging to generate one frame's worth of frame data from the plurality of pieces of frame data. Since a plurality of pieces of frame data with different patterns of speckle noise or artifacts are obtained by imaging a same location of an object using ultrasonic waves with different central frequencies, an ultrasonic image with reduced speckle noise or artifacts can be obtained by combining the plurality of pieces of frame data.

However, since frequency compound processing requires a plurality of scans (imaging at a plurality of central frequencies) as compared to normal processing in which an ultrasonic image is generated by only one scan (imaging at one central frequency), the frame rate declines. For example, when two scans are performed by changing the central frequency to f1 and f2 as described above, the frame rate drops to ½ as compared to normal processing in which an ultrasonic image is generated by only one scan. In addition, when the ultrasonic probe 102 or the object moves while performing the plurality of scans, since a position of the object in each piece of frame data deviates, combining such frame data may result in a decline in image quality such as resolution or contrast.

Estimation Calculating Block

The estimation calculating block 205 will be described. The estimation calculating block 205 performs processing for generating (estimating) a compound processing-equivalent image using a learned model.

Machine learning is favorably used in learning of a model. Examples of a specific algorithm for machine learning include a nearest neighbor method, a naive Bayes method, and a support vector machine. Another example is deep learning that autonomously generates a feature amount and a coupling weight coefficient for learning using a neural network. A usable algorithm among those described above can be appropriately used and applied to the present embodiment.

Figure 4:
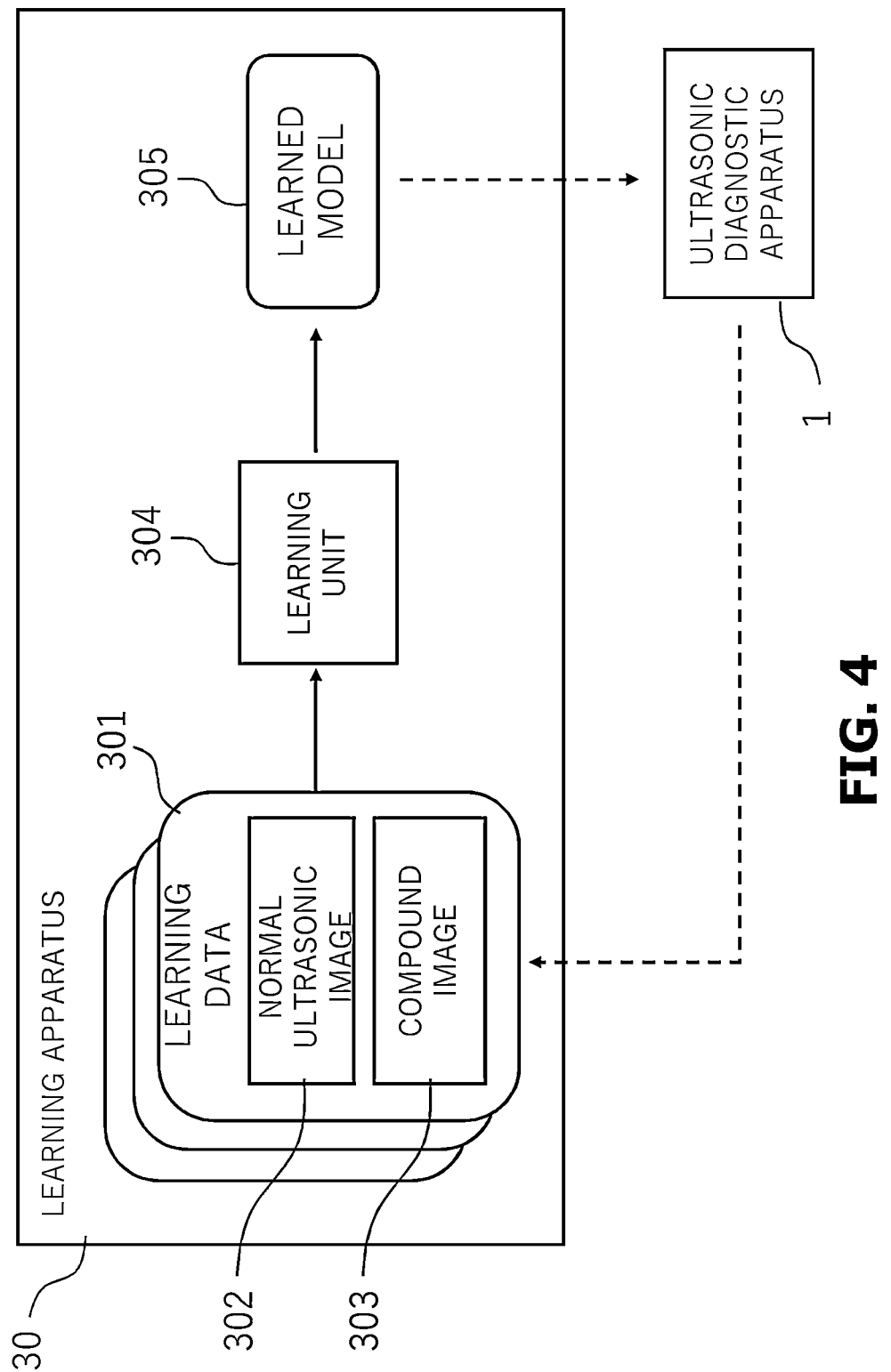
FIG. 4 is a block diagram showing an example of a learning apparatus.

FIG. 4 shows an example of a learning apparatus 40 that performs machine learning of a model. The learning apparatus 40 has a learning unit (a learner) 404 that carries out machine learning of a model using a plurality of pieces of learning data 401. The learning unit 404 may use any of the machine learning algorithms exemplified above or may use another machine learning algorithm. The learning data 401 is constituted by a pair of input data and ground truth data (teacher data). First data based on a first received signal that is obtained by one scan of an ultrasonic wave is used as the input data and, in the present embodiment, a normal ultrasonic image 402 is used as the first data. In addition, second data based on a second received signal that is obtained by a plurality of scans in which a transmission direction or a central frequency of the ultrasonic wave has been changed is used as the ground truth data and, in the present embodiment, a compound image 403 is used as the second data. The learning unit 404 learns a correlation between the normal ultrasonic image 402 and the compound image 403 based on the plurality of pieces of supplied learning data 401 and creates a learned model 405. Accordingly, the learned model 405 can acquire a function (a capability) of generating a compound processing-equivalent image as output data when a normal ultrasonic image is given as input data. The learned model 405 is mounted to a program to be executed by the estimation calculating block 205 of the ultrasonic diagnostic apparatus 1. Learning of a model (generation processing of the learned model 405) is desirably performed before being incorporated into the ultrasonic diagnostic apparatus 1. However, when the ultrasonic diagnostic apparatus 1 has a learning function, learning (new learning or additional learning) may be performed using image data obtained by the ultrasonic diagnostic apparatus 1.

FIG. 5 is a diagram explaining learning by the estimation calculating block 205 that outputs a spatial compound processing-equivalent image. FIG. 6 is a diagram explaining learning by the estimation calculating block 205 that outputs a frequency compound processing-equivalent image. Two types of learned models 405 including a model having been learned to output a spatial compound processing-equivalent image and a model having been learned to output a frequency compound processing-equivalent image may be incorporated into the ultrasonic diagnostic apparatus 1 or only one of the learned models 405 may be incorporated into the ultrasonic diagnostic apparatus 1. Alternatively, a single learned model 405 having been learned using both pieces of learning data shown in FIGS. 5 and 6 may be incorporated into the ultrasonic diagnostic apparatus 1.

Learning by the estimation calculating block 205 that outputs a spatial compound processing-equivalent image will now be described with reference to FIG. 5. In this case, a normal B-mode image of a given object or, in other words, an image having been imaged by forming an ultrasonic beam only in one direction without performing spatial compound processing is used as input data. In addition, a spatial compound image having been imaged using spatial compound processing of the same object is used as ground truth data.

FIG. 5 exemplifies three pieces of learning data with learning data IDs of ID1 to ID3. A normal B-mode image B1-1 is used as the input data of learning data ID1. In addition, a spatial compound image SC1-1 having been imaged using spatial compound processing of the same object is used as the ground truth data of learning data ID1. Compound conditions of the spatial compound image SC1-1 include 3 frames as the number of compounds and deflection angles of respective pieces of frame data of –10 degrees, 0 degrees, and 10 degrees. Learning data ID2 represents an example in which, with respect to the same input data (the normal B-mode image B1-1) as learning data ID1, a spatial compound image SC1-2 with different conditions of compound processing is used as the ground truth data. Compound conditions of the spatial compound image SC1-2 include 5 frames as the number of compounds and deflection angles of respective pieces of frame data of –15 degrees, –10 degrees, 0 degrees, 10 degrees, and 15 degrees. In this manner, with respect to the ultrasonic image B1-1 acquired under a condition that spatial compound processing is not performed on a given object, spatial compound images SC1-1 and SC1-2 obtained by imaging the same object using spatial compound processing are learned as ground truth data. In addition, learning data ID3 represents an example in which, using a normal B-mode image B2-1 of a different object from the pieces of learning data ID1 and ID2 as input data, a spatial compound image SC2-1 having been imaged using spatial compound processing is used as the ground truth data.

Learning by the estimation calculating block 205 that outputs a frequency compound processing-equivalent image will now be described with reference to FIG. 6. In this case, a normal B-mode image of a given object or, in other words, an image having been imaged using an ultrasonic wave with a single central frequency without performing frequency compound processing is used as input data. In addition, a frequency compound image having been imaged using frequency compound processing of the same object is used as ground truth data.

FIG. 6 exemplifies three pieces of learning data with learning data IDs of ID4 to ID6. The normal B-mode image B1-1 is used as the input data of learning data ID4. In addition, a frequency compound image FC1-1 having been imaged using frequency compound processing of the same object is used as the ground truth data of learning data ID4. Compound conditions of the frequency compound image FC1-1 include 2 frames as the number of compounds and transmission central frequencies of respective pieces of frame data of 2 MHz and 8 MHz. Learning data ID5 represents an example in which, with respect to the same input data (the normal B-mode image B1-1) as learning data ID4, a frequency compound image FC1-2 with different conditions of compound processing is used as the ground truth data. Compound conditions of the frequency compound image FC1-2 include 4 frames as the number of compounds and transmission central frequencies of respective pieces of frame data of 2 MHz, 4 MHZ, 6 MHz, and 8 MHz. In this manner, with respect to the ultrasonic image B1-1 acquired under a condition that frequency compound processing is not performed on a given object, frequency compound images FC1-1 and FC1-2 obtained by imaging the same object using frequency compound processing are learned as ground truth data. In addition, learning data ID6 represents an example in which, using a normal B-mode image B2-1 of a different object from the pieces of learning data ID4 and ID5 as input data, a frequency compound image FC2-1 having been imaged using frequency compound processing is used as the ground truth data.

As shown in FIGS. 5 and 6, learning is favorably performed using various pieces of learning data such as learning data representing different compound conditions and learning data representing different objects. Performing learning using as many pieces of learning data as possible enables learning to be performed with respect to input data of various patterns, and an image with favorable image quality can be expected to be estimated in a stable manner even during actual use. It should be noted that, as an object, any of a digital phantom that can be imaged by a transmission/reception simulation of ultrasonic waves, an actual phantom, and an actual living organism may be used.

In addition, preprocessing of learning data may be performed. For example, learning efficiency may be improved by correcting non-uniformity of brightness values due to attenuation of ultrasonic waves. Even in a compound image, an image of a portion where an ultrasonic beam converges in a favorable manner or, in other words, a vicinity of a depth at which a transmission focus has been set may be extracted and used. Accordingly, an improvement in resolution of an estimated image can be expected. Processing for removing a shadow caused by a separation of an ultrasonic probe during imaging of an object or the like from input data may be performed. Accordingly, stability of estimation accuracy can be improved. Alternatively, by using learning data in which both input data and ground truth data include a shadow caused by a separation of an ultrasonic probe or the like, an effect can be expected that an image enabling separation of the probe to be recognized be estimated by an estimated image when a separation of a probe actually occurs.

Figure 7:
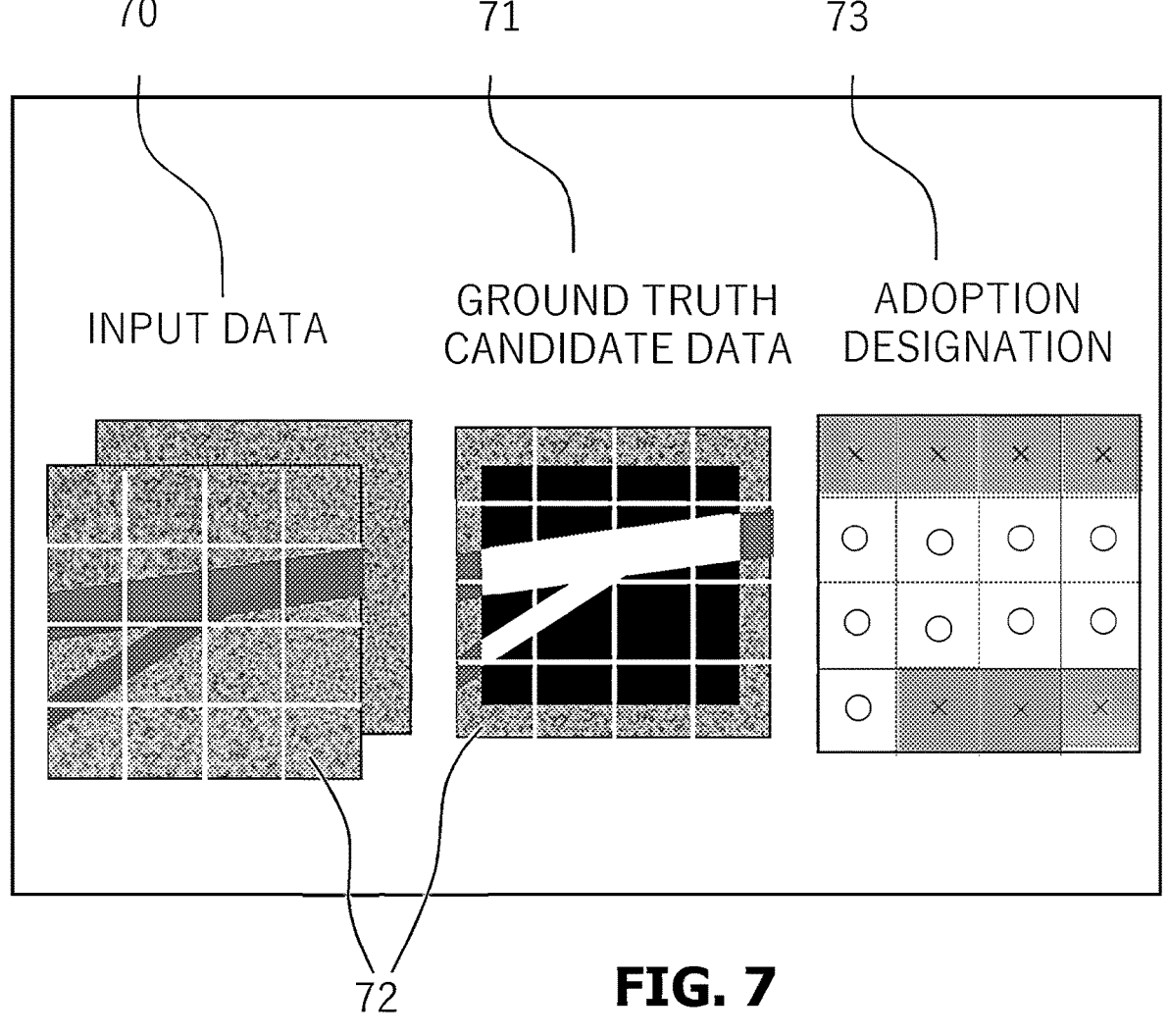
FIG. 7 is a diagram showing an example of a GUI for creating learning data.

In addition, in learning, preprocessing of input data and ground truth data may be further performed using a GUI such as that shown in FIG. 7. Input data 70 and ground truth candidate data 71 are shown in a display screen, and indicators 72 that divide each piece of data into a plurality of regions are displayed. In the example shown in FIG. 7, images are divided into 16 regions in a 4 by 4 arrangement. An adoption designation box 73 is a user interface that enables a user to designate whether to adopt or reject each region. The user enters "o" into a region to be adopted as learning data and "x" into a region to be excluded while comparing the input data 70 and the ground truth candidate data 71 with each other. Accordingly, locations where unexpected image deterioration has occurred in the ground truth candidate data 71 and the like can be excluded. For example, a location where it is determined that image quality has declined due to movement of an object while an ultrasonic beam had been transmitted and received a plurality of times during compound processing and the like can be excluded. While FIGS. 5 and 6 have been described on the assumption that an entire image is to be used as one piece of image data, when an image is divided into a plurality of regions as shown in FIG. 7, an image (a partial image) of each of the regions is used as one piece of learning data. In other words, in the example shown in FIG. 7, since there are nine regions to be adopted, nine sets of learning data are to be generated.

While a normal B-mode image is exemplified as input data in the present embodiment, related information other than a normal B-mode image may be added to input data. For example, adding information such as a transmission frequency and a band of a bandpass filter when acquiring a normal B-mode image to input data increases the possibility that accurate estimation can be performed in accordance with a state of the input data. In addition, information describing which portion of a living organism the object represents, which orientation the ultrasonic probe is in contact relative to a body axis, and the like may be added to input data. It is expected that estimation accuracy will further increase in correspondence to a feature of each site (for example, the presence of a surface fat layer, the presence of a high brightness region created by a fascial structure, or the presence of a low brightness region due to a thick blood vessel). Furthermore, by adding information such as a field of medicine, gender, BMI, age, and pathological condition to input data, there is a possibility that a learned model corresponding to the feature of each site described earlier in greater detail can be obtained and a further increase in estimation accuracy is expected.

In addition, the learned model 405 of the estimation calculating block 205 mounted to the ultrasonic diagnostic apparatus 1 may be a model having learned image data of all fields of medicine or a model having learned image data of each field of medicine. When a model having learned image data of each field of medicine is mounted, the system control block 109 may cause the user of the ultrasonic diagnostic apparatus 1 to input or select information regarding a field of medicine to change the learned model to be used in accordance with the field of medicine. It is expected that estimation accuracy will further increase by selectively using a model for each field of medicine in which imaging sites are limited to a certain degree.

The learned model 405 obtained by performing learning using a variety of such imaging conditions and a normal B-mode image as input data and a compound image as ground truth data operates on the estimation calculating block 205. As a result, it is expected that the estimation calculating block 205 will estimate and output an image corresponding to a compound image with high resolution or contrast with respect to the input normal B-mode image.

Image Generation Method

Next, details of processing for image generation according to the present embodiment will be described with reference to FIG. 1. An imaging instruction is input by the user using a GUI (not illustrated). The system control block 109 having received the instruction from the GUI inputs a transmission instruction of ultrasonic waves to the transmission electrical circuit 104. The transmission instruction favorably includes a parameter for calculating a delay time and sound velocity information. Based on the transmission instruction from the system control block 109, the transmission electrical circuit 104 outputs a plurality of pulse signals (voltage waveforms) to the plurality of transducers 101 of the ultrasonic probe 102 through the probe connecting unit 103. At this point, the transmission electrical circuit 104 sets a delay time of a pulse signal to be applied to each transducer 101 in accordance with a transmission direction (a deflection angle) and a focus position of the ultrasonic beam. In this case, an ultrasonic beam having a deflection angle θ1 as shown in FIG. 3 is adopted as a first transmission ultrasonic beam shape. It should be noted that a deflection angle is an angle formed between a normal direction of a surface on which the plurality of transducers 101 are arranged and an axial direction of the ultrasonic beam and, in the example shown in FIG. 3, it is assumed that θ1=0 degrees.

The ultrasonic waves transmitted from the plurality of transducers 101 propagate inside the object 100 and are reflected at a boundary of acoustic impedance inside the object 100. The plurality of transducers 101 receive reflected ultrasonic waves that reflect a difference in acoustic imped- ances and convert the reflected ultrasonic waves into a voltage waveform. The voltage waveform is input to the reception electrical circuit 105 through the probe connecting unit 103. The reception electrical circuit 105 amplifies and digitally samples the voltage waveform as necessary and outputs the voltage waveform as a received signal to the received signal processing block 106. In the received signal processing block 106 shown in FIG. 2, with respect to a received signal obtained by the reception electrical circuit 105, the phasing addition processing block 201 performs phasing addition based on an element arrangement and various conditions (aperture control, signal filtering) of image generation that are input from the system control block 109. The signal subjected to phasing addition is saved in the signal storage block 202. Accordingly, first received data corresponding to the first transmission ultrasonic beam is saved in the signal storage block 202. By performing similar processing, second received data corresponding to a second transmission ultrasonic beam having a deflection angle of θ2 and third received data corresponding to a third transmission ultrasonic beam having a deflection angle of θ3 as shown in FIG. 3 are saved in the signal storage block 202. In this case, it is assumed that θ2=−10 degrees and θ3=10 degrees.

Using the first, second, and third pieces of received data, the calculation processing block 203 generates an ultrasonic signal from which noise has been reduced by spatial com- pound processing. The signal is transmitted to the B-mode processing block 204. The B-mode processing block 204 performs envelope detection processing, logarithmic com- pression processing, and the like and generates a spatial compound image in which signal strength at each point inside the observation region is expressed by brightness intensity. In addition, the first received data is also trans- mitted to the B-mode processing block 204 and, by per- forming envelope detection processing, logarithmic com- pression processing, and the like, a normal B-mode image based on the first received data is generated. The estimation calculating block 205 inputs the normal B-mode image based on the first received data to a learned model and acquires a compound processing-equivalent image (herein- after, described as an "estimated image") that represents an estimation result of the learned model. The spatial com- pound image and the estimated image are input to the image processing block 107. The image processing block 107 applies brightness adjustment, interpolation, and other fil- tering on each of the spatial compound image and the estimated image.

In this case, a normal B-mode image based on first received data with a deflection angle of 0 degrees is used as an input to the estimation calculating block 205. The reason for this is to ensure that a region of the estimated image output from the estimation calculating block 205 and a region of the spatial compound image generated by the B-mode processing block 204 are the same. In other words, by generating an estimated image from a normal B-mode image based on first received data with a deflection angle of 0 degrees, there is an advantage that processing such as positioning or region matching between the estimated image and the spatial compound image can be omitted. However, an estimated image may be generated from a normal B-mode image based on the second received data or the third received data. In doing so, since there is a deviation in regions between the estimated image and the spatial com- pound image, a common region shared by both images may be cut out and displayed. Alternatively, a different part of the estimated image and the spatial compound image may be complemented by the normal B-mode image.

Next, a control example of generation and display of an image in the ultrasonic diagnostic apparatus 1 will be described. The ultrasonic diagnostic apparatus 1 has at least any of the following display modes: a mode in which a display image is updated using only a compound image; a mode in which a display image is updated using only an estimated image; and a mode in which a display image is updated using both a compound image and an estimated image. When the ultrasonic diagnostic apparatus 1 has a plurality of display modes, for example, the user is favorably able to switch among the display modes.

Figure 8:
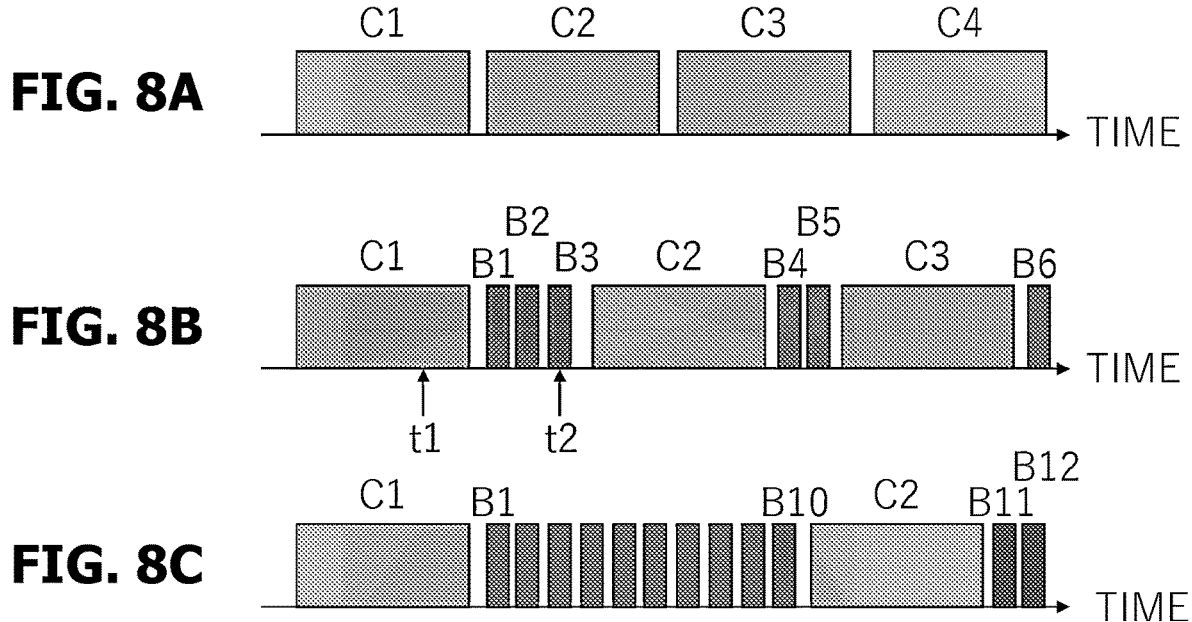
FIGS. 8A to 8C are diagrams representing a time sequence according to the first embodiment.

FIGS. 8A to 8C show an example of timings of formation of an estimated image from a normal B-mode image and formation of a compound image by compound processing in the estimation calculating block 205. FIG. 8A represents an example of a display mode in which a display image is updated using only the compound image and FIGS. 8B and 8C represent an example of a display mode in which a display image is updated using both the compound image and the estimated image. In addition, FIG. 9 is a flow chart showing an example of switching processing between formation of an estimated image and formation of a compound image in the display modes shown in FIGS. 8A and 8B.

FIG. 8A shows timings of generation and display of an image by compound processing. C1, C2, C3, and C4 denote times required for scanning an observation region a plurality of times by ultrasonic beams of a plurality of patterns with different deflection angles, performing compound processing, and displaying a compound image (a frame). In this case, four compound images are to be output.

Hereinafter, a description will be given with reference to the flow chart shown in FIG. 9. The apparatus is switched to a control mode shown in the flow chart according to an instruction from the user, a default setting of the apparatus, or a field of medicine or a user ID. It should be noted that the processing shown in FIG. 9 is realized as the respective units s 101 to 108 of the ultrasonic diagnostic apparatus 1 operate under control of the system control block 109.

In step S90, a compound image is generated and displayed. Specifically, an observation region is scanned a plurality of times by ultrasonic beams of a plurality of patterns with different deflection angles, compound processing is performed, one frame's worth of a compound image is generated, and the compound image is displayed on the display apparatus 108. A time required by the operation is denoted by C1 in FIG. 8B. It should be noted that the system control block 109 has a frame memory and is capable of temporarily saving display image data that is output from the received signal processing block 106.

In step S91, an estimated image is generated from a normal B-mode image. Specifically, a normal B-mode image is created by performing transmission/reception of an ultrasonic beam in only one direction of which the deflection angle is 0 degrees and an estimated image is generated by the estimation calculating block 205. A time required by the operation is denoted by B1 in FIG. 8B.

In step S92, the system control block 109 evaluates whether or not the estimated image generated by the estimation calculating block 205 satisfies a prescribed condition. A purpose of the evaluation is to determine whether or not reliability of the estimated image (accuracy of estimation) is high and, in the present embodiment, it is assumed that the higher a correlation with a last display image stored in the frame memory, the higher the reliability. Metrics for evaluating correlation may be designed in any way. In the present embodiment, for example, a correlation strength is evaluated using an inverse of an SSD (a sum of squares of a difference in pixel values) between the estimated image and a last display image. When the correlation is at least a prescribed threshold or, in other words, when the estimated image has not changed significantly from the last display image, validity or reliability of the estimated image is assumed to be high and, in step S93, the system control block 109 updates the display image using the estimated image. For example, the system control block 109 may generate a new display image by combining the last display image and the present estimated image with a prescribed weight. Alternatively, the system control block 109 may adopt the present estimated image as the new display image as-is (it can be considered that a weight of the last display image is 0 and a weight of the estimated image is 1). Alternatively, the system control block 109 may generate a new display image by combining the last compound image and the present estimated image with a prescribed weight. In step S94, the display image generated in step S93 is displayed on the display apparatus 108.

In step S95, the system control block 109 checks whether or not the number of times the estimated image was consecutively used to update the display image has reached a prescribed number of times N (in the present example, it is assumed that N=10). When the number of times is smaller than N, a return is made to step S91 where imaging of a normal B-mode image is performed and an estimated image is generated (B2 in FIG. 8B denotes a time required by this operation). Subsequently, processing of steps S92 to S95 is repeated.

When the correlation between the estimated image and the last display image falls below the prescribed threshold while the processing is being repeated, the system control block 109 does not use the estimated image for display and switches control to generating and displaying a new compound image (step S90). FIG. 8B represents an example in which, since the estimated image obtained at time B3 had a low correlation with the last display image, a new compound image has been generated at time C2. Once a compound image is displayed, a switch is made to control for once again generating an estimated image (step S91).

In addition, in step S95, when it is determined that the number of times the estimated image was consecutively used to update the display image has reached N times, the system control block 109 stops generation of the estimated image and switches control to generating and displaying a new compound image (step S90). FIG. 8C represents an example in which, since the number of times the estimated image was consecutively used has reached 10 times (B1 to B10), a new compound image has been generated at time C2.

According to the control described above, since an estimated image generated from a B-mode image obtained in one scan is used to update a display image, image display can be realized at a higher frame rate than when updating the display image using only the compound image. As is apparent from a comparison between FIG. 8A (a display mode in which only a compound image is used) and FIG. 8B (a display mode in which both a compound image and an estimated image are used), it is shown that a larger number of frames can be displayed per unit time in the latter case. In addition, in the present embodiment, since control to switch to generating and displaying a compound image is performed when reliability of an estimated image declines, the possibility of displaying an image with low image quality or an image that represents a failed estimation can be suppressed. Furthermore, in the present embodiment, since processing for using an estimated image to update a last compound image or a last display image is performed instead of using the estimated image itself for display, image display with high reliability as a whole can be continued.

When calculating a correlation, a correlation between entire observation regions need not be used and a determination may be made based on, after dividing an observation region and calculating respective correlations of the divided regions, whether or not a correlation is at least a certain level in a certain percentage of the divided regions. By performing such control, for example, when imaging a heart, since a correlation of other regions remain high even though a correlation of a region containing a moving valve declines, display at a high frame rate using an estimated image can be continued. In addition, while a correlation between an estimated image and a last display image is evaluated in the processing shown in FIG. 9, alternatively, a correlation between an estimated image and a last compound image may be evaluated.

In addition, while an image used to evaluate a correlation and an image used for display are the same in the processing shown in FIG. 9, different images may be used between the evaluation of a correlation and the display. For example, only an image in a partial region (referred to as a selected region) among the observation region may be used to evaluate a correlation, and generation of an image of the entire observation region may be controlled according to the evaluation of the image in the selected region. Accordingly, efficiency of imaging and image processing can be improved. It should be noted that the selected region may be arbitrarily set and, for example, a region constituting 1/n (where n is an integer of at least 2) of the observation region or a central region of the observation region may be mechanically set as the selected region or the user may be enabled to set the selected region.

Figure 10:
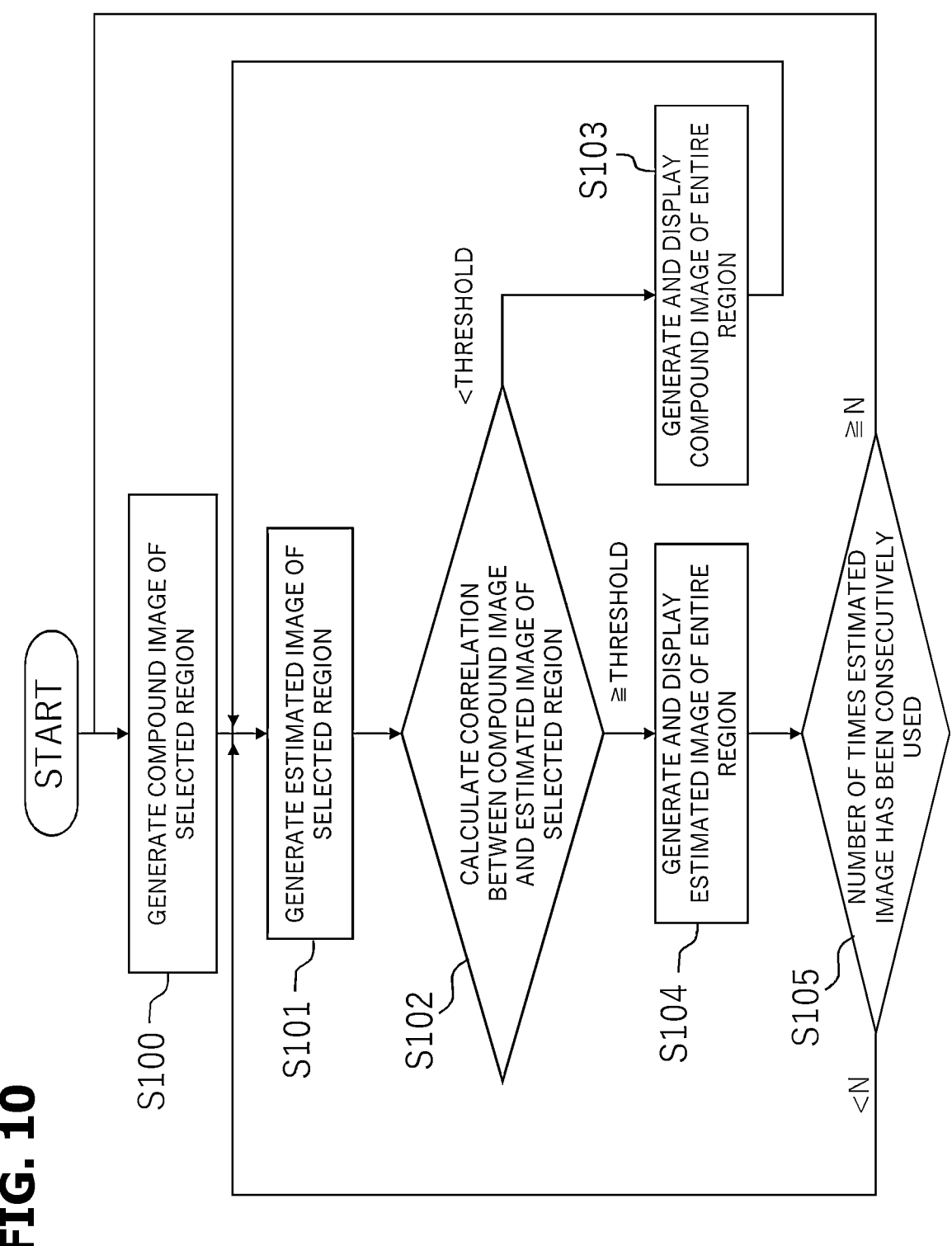
FIG. 10 is a diagram representing a flow of processing according to the first embodiment.

FIG. 10 shows an example of control for using an image in the selected region for estimating a correlation. In step S100, only a selected region is scanned a plurality of times by ultrasonic beams of a plurality of patterns with different deflection angles and a compound image of the selected region is generated by compound processing. This image is not used for display. In step S101, a normal B-mode image of the selected region is imaged and an estimated image of the selected region is calculated from the normal B-mode image. In step S102, the system control block 109 calculates a correlation between the compound image of the selected region and the estimated image of the selected region. When the correlation is lower than a threshold, in step S103, a compound image of the entire observation region is generated and displayed. Subsequently, a return is made to step S101. On the other hand, when correlation between the compound image and the estimated image of the selected region is at least the threshold, in step S104, a normal B-mode image of the entire observation region is imaged and an estimated image of the entire observation region is generated from the normal B-mode image and displayed. Steps S101 to S104 are repeated until the number of times the estimated image was consecutively used reaches N times, and once the number of times reaches N times, a return is made to step S100 (step S105). By performing such control, since the time required to acquire images (a compound image and an estimated image) to be used to evaluate a correlation can be significantly reduced, efficiency of processing can be improved.

Next, control in a case where an instruction to save a still image or a moving image is issued by the user during an imaging operation will be described. When receiving an instruction to save a still image, the system control block 109 may save a compound image and/or an estimated image acquired at a time point that is closest to a timing at which the instruction had been received. At this point, images having been acquired but not used for display may be excluded from objects to be saved. For example, when an instruction to save a still image is input to the system control block 109 through a GUI or the like at a timing t1 shown in FIG. 8B, the compound image acquired at time C1 and the estimated image acquired at time B1 are saved. In this case, the two images may be presented to the user as candidates to be saved and the user may be asked to select an image to be actually saved. In addition, for example, when an instruction to save a still image is input at a timing t2, the compound image acquired at time C2 and the estimated image acquired at time B2 which is a time point that is closest to the timing t2 and which is also an estimated image having been used for display are saved. Since the estimated image obtained at time B3 has a correlation that is lower than the threshold and the estimated image has not been used for display, the estimated image is excluded from objects to be saved. With respect to saving the images, a setting that causes only compound images to be saved or only estimated images to be saved can be separately configured as an option of the system. Furthermore, when a save instruction is issued, the flow chart shown in FIG. 9 or 10 may be interrupted to perform control for imaging a compound image and the obtained image may be saved.

In addition, with respect to saving a moving image, a compound image and an estimated image may be saved separately or saved in a mixed manner. Switching between these save methods can also be set as an option of the system. Furthermore, since a frame rate of an image changes depending on control in the image generation method according to the present embodiment, when saving a moving image, interpolation and processing may be applied so as to create data at constant time intervals and a moving image with a constant frame rate may be subsequently saved.

While control for adaptively switching between a compound image and an estimated image based on a correlation of images has been described in the present embodiment, a ratio of the images may be fixed or the system control block 109 may perform control so that the ratio can be interactively changed by the user from a GUI. In addition, when there are consecutive estimated images and a correlation between estimated images that are separated from each other by at least one estimated image is high, a determination may be made that an object has hardly moved and a switch to a compound image may be automatically made. Accordingly, an image acquired by compound processing can be obtained with respect to the object that has hardly moved.

Figures 11A, 11B, 11C:
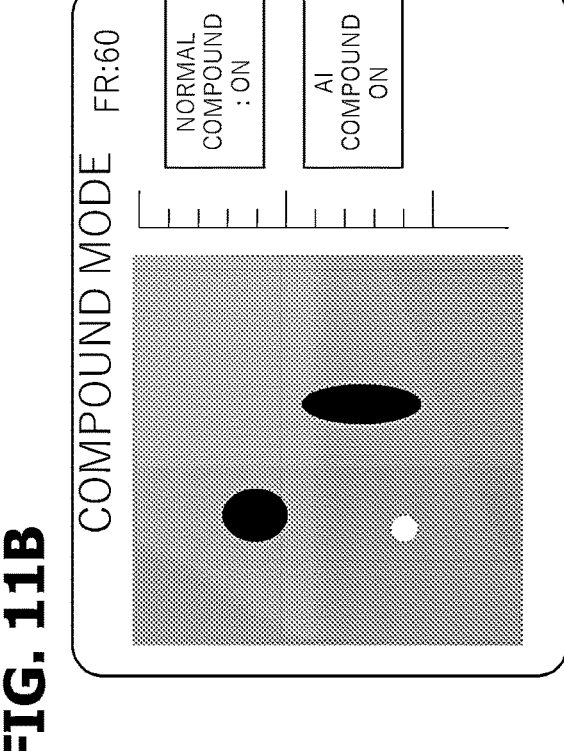
FIGS. 11A to 11C are diagrams representing an example of display by a display apparatus according to the first embodiment.

FIGS. 11A to 11C schematically show a display example of an image on the display apparatus 108. FIG. 11A represents a display of a compound image created by compound processing (normal compound: ON, AI compound: OFF, corresponds to FIG. 8A). A frame rate (FR) is set to 35 fps. It should be noted that a "normal compound" button and an "AI compound" button are toggle buttons and the user can switch between ON and OFF by depressing the buttons. When "normal compound" is ON, a compound image is used to update a display image, and when "normal compound" is OFF, a compound image is not used to update a display image. In addition, when "AI compound" is ON, an estimated image is used to update a display image, and when "AI compound" is OFF, an estimated image is not used to update a display image. In other words, the GUI enables the user to arbitrarily switch between display modes (types of images to be used to update a display image).

FIG. 11B represents a state where both a compound image and an estimated image from a normal B-mode image are appropriately switched and being displayed (normal compound: ON, AI compound: ON, corresponds to FIGS. 8B and 8C). As described earlier, using an estimated image increases the frame rate as compared to a case where only a compound image is displayed. In the example shown in FIG. 11B, the frame rate (FR) is set to 60 fps. Since the estimated image output from the estimation calculating block 205 is not an image created by directly imaging a received ultrasonic wave but includes estimation, the fact that the image is estimated is favorably displayed in the display region. In the present embodiment, displaying "AI compound: ON" in characters in the display region indicates that an estimated image is included in the display image. The indicator need not be characters and methods such as changing a color of an outer edge of a display image or a display region, causing the outer edge to blink, and changing a color, chroma, or a pattern of a background of the display image or the display region may be adopted.

In addition, FIG. 11C is an example in which a compound image and an estimated image from a normal B-mode image are displayed side by side. Only the compound image is displayed on a left side of a screen at a frame rate of 35 fps, and only the estimated image is displayed on a right side of the screen at a frame rate of 80 fps. Using the display screen enables the user to not only confirm the estimated image but also simultaneously confirm the compound image as ground truth data. Such a display screen is useful when evaluating or checking accuracy and reliability of the estimation calculating block 205.

While spatial compound processing has been explained as an example in the embodiment described above, similar control can be applied in a case of frequency compound processing.

Second Embodiment

Next, another embodiment of the present invention will be described. While a compound image and an estimation result of the estimation calculating block 205 have been used in combination in the first embodiment, in the second embodiment, only an estimation result of the estimation calculating block 205 is to be displayed without performing compound processing. Accordingly, an image with an image quality that is equivalent to compound processing can be displayed at a higher frame rate than in the first embodiment.

An overall configuration of the ultrasonic diagnostic apparatus 1 is the same as that of the first embodiment (FIG. 1). A flow from transmitting an ultrasonic wave with respect to the object 100 up to inputting a received signal to the received signal processing block is similar to that of the first embodiment.

Figure 12:
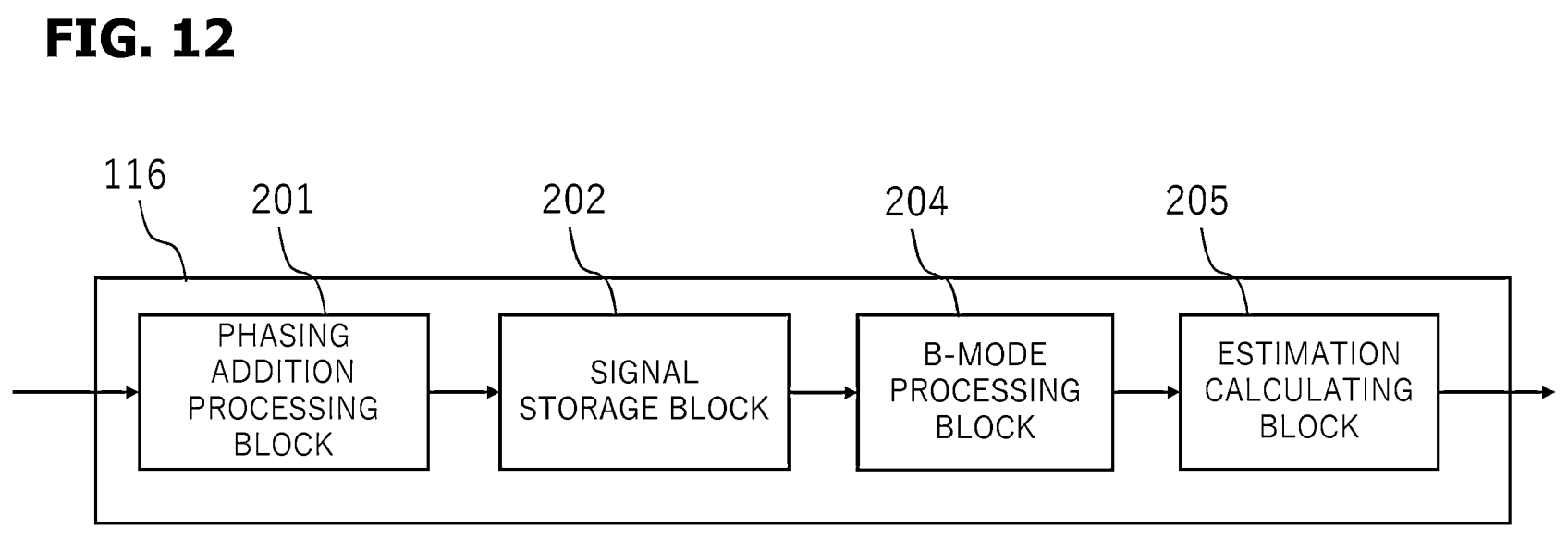

FIG. 12 is a diagram showing details of a received signal processing block 116 according to the second embodiment. The received signal processing block 116 according to the second embodiment has a phasing addition processing block 201, a signal storage block 202, a B-mode processing block 204, and an estimation calculating block 205. Functions and processing of each block are basically the same as the block with the same name in the first embodiment. In other words, a received signal loaded from the reception electrical circuit 105 is subjected to phasing addition by the phasing addition processing block 201 and saved in the signal storage block 202. Subsequently, the B-mode processing block 204 generates a normal B-mode image and inputs the normal B-mode image to the estimation calculating block 205. The estimation calculating block 205 inputs the normal B-mode image to a learned model and obtains a compound processing-equivalent image (an estimated image) as an estimation result. In the present embodiment, the estimated image is used for display on the display apparatus 108.

Figure 13:
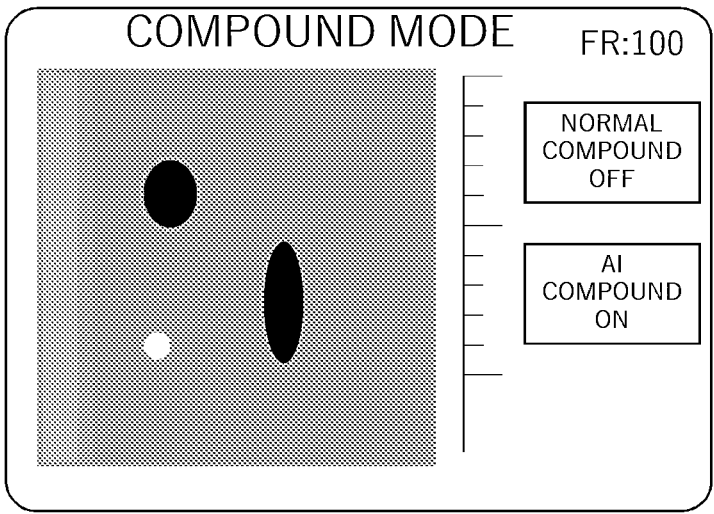
FIG. 13 is a diagram representing an example of display by a display apparatus according to the second embodiment.

FIG. 13 schematically shows a display example of an image according to the second embodiment. FIG. 13 represents a state where only an estimated image from a normal B-mode image is displayed (normal compound: OFF, AI compound: ON). As described earlier, displaying only an estimated image increases the frame rate as compared to the case of the first embodiment.

Third Embodiment

A third embodiment of the present invention will be described. FIG. 1 is a block diagram showing an example of a hardware configuration of an ultrasonic diagnostic apparatus.

In general, the ultrasonic diagnostic apparatus 1 has an ultrasonic probe (an ultrasonic transducer) 102, a probe connecting unit 103, a transmission electrical circuit 104, a reception electrical circuit 105, a received signal processing block 106, an image processing block 107, a display apparatus 108, and a system control block 109. The ultrasonic diagnostic apparatus 1 is a system for transmitting an ultrasonic pulse to an object 100 from the ultrasonic probe 102, receiving reflected ultrasonic waves having been reflected inside the object 100, and generating image information (an ultrasonic image) of the inside of the object 100. The ultrasonic image obtained by the ultrasonic diagnostic apparatus 1 is to be used in various clinical examinations.

The ultrasonic probe 102 is a probe adopting an electronic scan system and has a plurality of transducers 101 arranged one-dimensionally or two-dimensionally at a tip thereof. The transducer 101 is an electric mechanical conversion element that performs mutual conversion between an electric signal (a voltage pulse signal) and an ultrasonic wave (an acoustic wave). The ultrasonic probe 102 transmits ultrasonic waves from the plurality of transducers 101 to the object 100 and receives reflected ultrasonic waves from the object 100 by the plurality of transducers 101. Reflected acoustic waves reflect a difference in acoustic impedances inside the object 100.

The transmission electrical circuit 104 is a transmitting unit that outputs a pulse signal (a drive signal) with respect to the plurality of transducers 101. By applying a pulse signal with a time difference with respect to the plurality of transducers 101, ultrasonic waves with different delay times are transmitted from the plurality of transducers 101 and a transmission ultrasonic beam is formed. By selectively changing the transducer 101 to which the pulse signal is applied (in other words, the transducer 101 to be driven) and changing a delay time (an application timing) of the pulse signal, a direction and a focus of the transmission ultrasonic beam can be controlled. An observation region inside the object 100 is scanned by sequentially changing the direction and the focus of the transmission ultrasonic beam. By transmitting a pulse signal with a prescribed driving waveform to the transducers 101, the transmission electrical circuit 104 generates a transmission ultrasonic wave having a prescribed transmission waveform in the transducers 101. The reception electrical circuit 105 is a receiving unit that inputs, as a received signal, an electric signal output from the transducer 101 having received a reflected ultrasonic wave. The received signal is input to the received signal processing block 106. Operations of the transmission electrical circuit 104 and the reception electrical circuit 105 or, in other words, transmission/reception of ultrasonic waves is controlled by the system control block 109. It should be noted that, in the present specification, both an analog signal output from the transducers 101 and digital data obtained by sampling (digitally converting) the analog signal will be referred to as a received signal without particular distinction. However, a received signal may sometimes be described as received data depending on the context in order to clearly indicate that the received signal is digital data.

The received signal processing block 106 is an image generating unit that generates image data based on a received signal obtained from the ultrasonic probe 102. The image processing block 107 applies image processing such as brightness adjustment, interpolation, and filter processing on the image data generated by the received signal processing block 106. The display apparatus 108 is a display unit for displaying image data and various kinds of information and is constituted by, for example, a liquid crystal display or an organic EL display. The system control block 109 is a control unit that integrally controls the transmission electrical circuit 104, the reception electrical circuit 105, the received signal processing block 106, the image processing block 107, the display apparatus 108, and the like.

Configuration of Received Signal Processing Block

FIG. 2 is a block diagram showing an example of functions included in the received signal processing block 106. The received signal processing block 106 has a phasing addition processing block 201, a signal storage block 202, a calculation processing block 203, a B-mode processing block 204, and an estimation calculating block 205.

The phasing addition processing block 201 performs phasing addition on received signals obtained from the reception electrical circuit 105 and saves the added received signal in the signal storage block 202. Phasing addition processing refers to processing for forming a received ultrasonic beam by varying a delay time for each transducer 101 and adding up received signals of the plurality of transducers 101 and is also called Delay and Sum (DAS) beamforming. The phasing addition processing is performed by the phasing addition processing block based on an element arrangement and various conditions of image generation (aperture control and signal filtering) that are supplied from the system control block 109.

The calculation processing block 203 generates an ultrasonic signal based on a harmonic component using a conventional tissue harmonic imaging (THI) method. The received signal saved in the signal storage block 202 and the ultrasonic signal for THI are transmitted to the B-mode processing block 204. The calculation processing block 203 corresponds to the calculation processing unit according to the present invention.

The B-mode processing block 204 performs envelope detection processing and logarithmic compression processing on the received signal and the ultrasonic signal for THI from the signal storage block 202 and the calculation processing block 203 and generates image data in which signal strength at each point inside the observation region is expressed by brightness intensity.

The estimation calculating block 205 (the estimation calculating unit) uses a model to estimate data that is obtained by transmission/reception of ultrasonic waves with a plurality of different transmission waveforms from third data that is obtained by transmission/reception equivalent to transmission/reception of an ultrasonic wave with one transmission waveform by the ultrasonic probe. In the present embodiment, the estimation calculating block 205 uses a learned model which is obtained by machine learning based on a received signal to estimate (generate) a pseudo-THI-equivalent image from a B-mode image based on the received signal saved in the signal storage block 202. The estimation calculating block 205 corresponds to the estimation calculating unit according to the present invention.

In the present specification, a "THI image" signifies an image generated from an ultrasonic signal for THI. A THI image can be considered an image generated using a conventional THI imaging method. In addition, a "pseudo-THI image" signifies an image equivalent to a THI image that is obtained by applying image processing (estimation calculation processing) on a B-mode image based on a received signal. Generation of a pseudo-THI image by the estimation calculating block 205 can be called THI image estimation processing. In addition, in order to clearly distinguish a THI image obtained by a conventional method from a pseudo-THI image, a THI image obtained by a conventional method may also be referred to as a normal THI image.

The received signal processing block 106 outputs a normal B-mode image, a normal THI image and a pseudo-THI image to the image processing block 107. The received signal processing block 106 does not always output all of these images and may output any of these images. The images to be output from the received signal processing block 106 are subjected to prescribed processing by the image processing block 107 and subsequently displayed by the display apparatus 108.

The received signal processing block 106 may be constituted by at least one processor and a memory. In this case, functions of the respective blocks 201 to 205 shown in FIG. 2 are to be realized by a computer program. For example, the functions of the respective blocks 201 to 205 can be provided by having a CPU load and execute a program stored in the memory. Other than the CPU, the received signal processing block 106 may include a processor (a GPU, an FPGA, or the like) responsible for operations of the calculation processing block 203 and operations of the estimation calculating block 205. In particular, an FPGA is effectively used in the calculation processing block 203 to which a large amount of data is input at the same time and a GPU is effectively used when executing operations in an efficient manner as in the estimation calculating block 205. The memory favorably includes a memory for storing a program in a non-transitory manner, a memory for temporarily saving data such as a received signal, and a working memory to be used by the CPU.

THI Imaging: Pulse Inversion Method

The pulse inversion (PI) method that is an image generation method in THI imaging will now be described. THI imaging is a method of generating an image based on a harmonic component by reducing a fundamental frequency component of a transmission ultrasonic wave from a plurality of received signals obtained by transmission/reception of ultrasonic waves having different transmission waveforms.

Figures 14A, 14B, 14C:
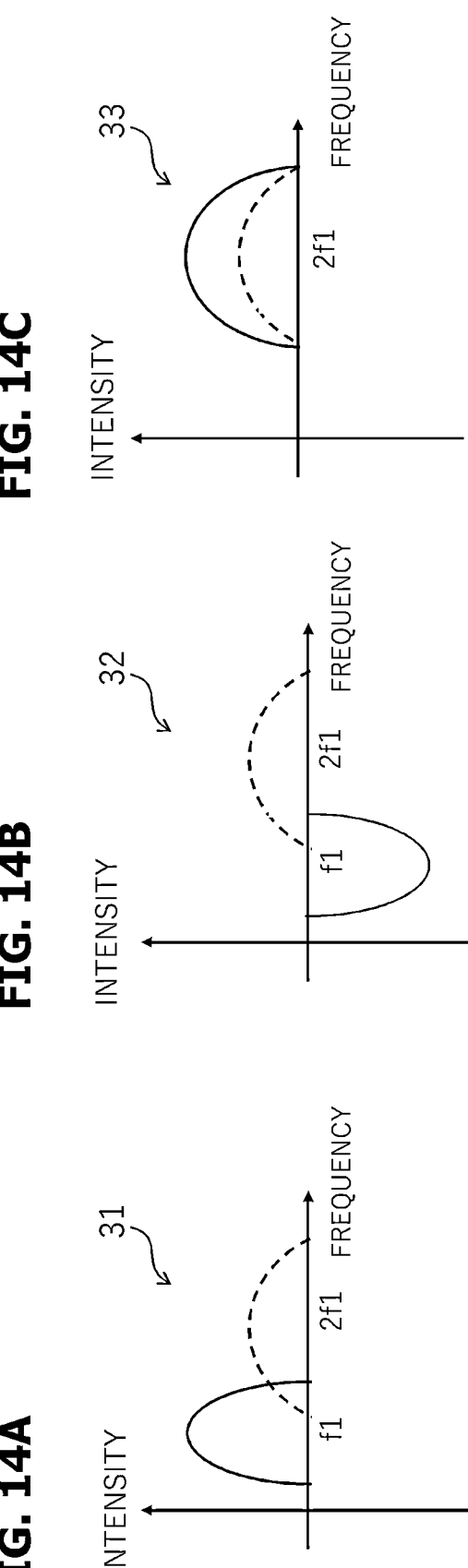
FIGS. 14A to 14C are diagrams illustrating extraction of a harmonic component in tissue harmonic imaging.

When an ultrasonic wave having a fundamental wave component f1 is transmitted to an object, as shown in FIG. 14A, a first received signal 31 representing a reflected ultrasonic wave including the fundamental wave component f1 and a harmonic component 2f1 is received. Adjusting the fundamental wave component f1 and the harmonic component 2f1 so as to be included in an effective frequency band of the ultrasonic probe 102 enables both the fundamental wave component f1 and the harmonic component 2f1 to be received. A frequency of a fundamental wave is generally lower than a central frequency of the ultrasonic probe 102.

The first received signal 31 is subjected to phasing addition in the received signal processing block 106 and saved in the signal storage block 202.

Next, as shown in FIG. 14B, when an ultrasonic wave having a frequency spectrum of which a phase has been inverted with respect to the first transmission waveform is transmitted to the object, a second received signal 32 representing a reflected ultrasonic wave including the fundamental wave component f1 and the harmonic component 2/1 is received. The second received signal 32 is subjected to phasing addition in the received signal processing block 106 and saved in the signal storage block 202.

A phase change of a second harmonic is twice a phase change of a fundamental wave. Therefore, when the phase of the fundamental wave is changed by 180 degrees (inverted), the phase of the second harmonic changes by 360 degrees. In other words, the harmonic components 2/1 included in the first received signal 31 and the second received signal 32 are in phase.

The received signals 31 and 32 subjected to phasing addition are added up by the calculation processing block 203. As a result, as shown in FIG. 14C, an ultrasonic signal 33 is generated which has a frequency spectrum in which the fundamental wave component f1 is canceled and the harmonic component 2/1 is enhanced. The ultrasonic signal 33 corresponds to the ultrasonic signal for THI described earlier.

The B-mode processing block 204 performs envelope detection processing, logarithmic compression processing, and the like with respect to the ultrasonic signal 33 generated by the calculation processing block 203 and generates image data in which signal strength at each point inside the observation region is expressed by brightness intensity. Accordingly, since only the harmonic component has been imaged, an image with superior resolution or contrast is obtained as compared to a normal B-mode in which a fundamental wave component is imaged.

While an example in which the number of transmissions/receptions of an ultrasonic signal is two has been described herein, the number of transmissions/receptions is not limited to two and may be any number of at least two as long as a phase of a transmission waveform is adjusted so as to cancel a fundamental wave component after having been added up. Although the fundamental wave component is ideally completely canceled, the fundamental wave component need not be completely canceled and need only be reduced by addition.

B-mode images can also be respectively generated from the first received signal 31 and the second received signal 32 described above. Since the B-mode images generated in this manner are based on a fundamental wave of a transmission ultrasonic wave, the B-mode images will also be called "fundamental wave images" in the present specification. In addition, a B-mode image based on the first received signal 31 will also be called a fundamental wave image in a THI positive pulse mode or a first fundamental wave image, and a B-mode image based on the second received signal 32 will also be called a fundamental wave image in a THI negative pulse mode or a second fundamental wave image.

Each of the first received signal 31 and the second received signal 32 can be referred to as a received signal obtained by transmission/reception of an ultrasonic wave with one transmission waveform. The first and second fundamental wave images can each be referred to as data based on a received signal obtained by transmission/reception of an ultrasonic wave with one transmission waveform. In addition, the first received signal 31 and the second received signal 32 as a whole can be referred to as a plurality of received signals respectively representing reflected ultrasonic waves generated by a plurality of transmissions of ultrasonic waves of which phases of transmission waveforms have been differentiated. The ultrasonic signal 33 for THI can be referred to as a signal obtained by reducing a fundamental frequency component and enhancing a harmonic component of a transmission ultrasonic wave from the plurality of received signals. In addition, an ultrasonic image (a THI image) based on the ultrasonic signal 33 can be referred to as harmonic image data based on the fundamental frequency component of the transmission ultrasonic wave included in the plurality of received signals.

Estimation Calculating Block

The estimation calculating block 205 will be described. The estimation calculating block 205 performs processing for generating (estimating) a pseudo-THI image using a learned model.

The model is machine-learned using learning data that includes first data (input data) based on a received signal obtained by transmission/reception of an ultrasonic wave with one transmission waveform and second data (ground truth data) based on received signals obtained by transmission/reception of ultrasonic waves with a plurality of different transmission waveforms. Examples of a specific algorithm for machine learning include a nearest neighbor method, a naive Bayes method, and a support vector machine. Another example is deep learning that autonomously generates a feature amount and a coupling weight coefficient for learning using a neural network. A usable algorithm among those described above can be appropriately used and applied to the present embodiment.

Figure 15:
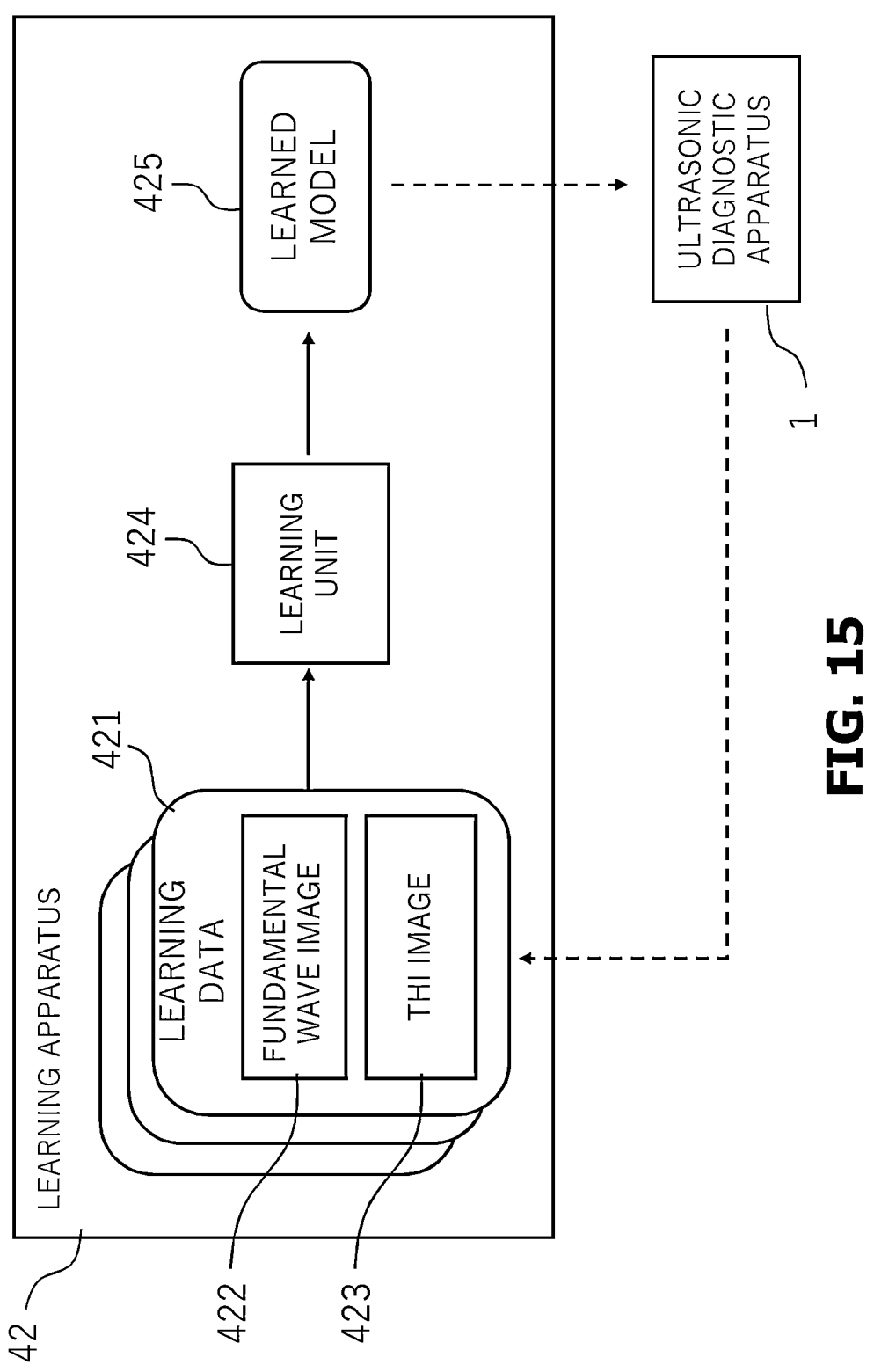
FIG. 15 is a diagram showing an example of a learning apparatus for learning a learning model.

FIG. 15 shows an example of a learning apparatus 42 that performs machine learning of a model. The learning apparatus 42 has a learning unit (a learner) 424 that carries out machine learning of a model using a plurality of pieces of learning data 421. The learning unit 424 may use any of the machine learning algorithms exemplified above or may use another machine learning algorithm. The learning data 421 is constituted by a pair of input data and ground truth data (teacher data). In the present embodiment, a fundamental wave image 422 (an image based on a received signal obtained by transmission/reception of an ultrasonic wave with one transmission waveform) is used as input data and a THI image 423 (an image based on a plurality of received signals obtained by transmission/reception of ultrasonic waves with a plurality of different transmission waveforms) is used as ground truth data. The learning unit 424 learns a correlation between the fundamental wave image 422 and the THI image 423 based on the plurality of pieces of supplied learning data 421 and creates a learned model 425. Accordingly, the learned model 425 can acquire a function (a capability) of generating a pseudo-THI image as output data when a fundamental wave image is given as input data. In other words, the learned model 425 acquires, from data based on a received signal obtained by transmission/reception of an ultrasonic wave with one transmission waveform, a function of estimating data based on a harmonic component of a transmission ultrasonic wave included in the received signal. The learned model 425 is mounted to a program to be executed by the estimation calculating block 205 of the ultrasonic diagnostic apparatus 1. Learning of a model (generation processing of the learned model 425) is desirably performed before being incorporated into the ultrasonic diagnostic apparatus 1. However, when the ultrasonic diagnostic apparatus 1 has a learning function, learning (new learning or additional learning) may be performed using image data obtained by the ultrasonic diagnostic apparatus 1.

The learning data may be prepared by generating a THI image using processing described with respect to the calculation processing block 203 and the B-mode processing block 204. Specifically, a plurality of received signals are acquired by performing a plurality of transmissions of ultrasonic waves of which phases have been differentiated, and a THI image based on harmonic components extracted from the plurality of received signals is generated. In addition, a B-mode image (a fundamental wave image) is generated from each of the received signals. A fundamental wave image generated in this manner and a waveform (a phase) of a transmission ultrasonic wave are used as input data and a THI image is used as ground truth data. Therefore, a plurality of sets of learning data are obtained as a result of one operation of THI imaging. It should be noted that generation of learning data may be performed by an apparatus other than an ultrasonic diagnostic apparatus to which a learning model is mounted or by the ultrasonic diagnostic apparatus to which the learning model is mounted.

The learning data will now be described in greater detail with reference to FIG. 16. Correct answer data included in the learning data is a THI image having been imaged using a THI mode. Among input data included in the learning data, a transmission waveform mode represents that a transmission ultrasonic wave used when generating a fundamental wave image which is input data has either a mode of transmitting a waveform without an inversion or a mode of transmitting a waveform with an inversion in the PI method. The mode of transmission without inversion is referred to as a THI positive pulse mode (or, simply, a positive pulse mode) and the mode of transmission with inversion is referred to as a THI negative pulse mode (or, simply, a negative pulse mode). Among input data included in the learning data, the fundamental wave image is data obtained by imaging a received signal corresponding to each transmission waveform (a fundamental wave image in the positive pulse mode or a fundamental wave image in the negative pulse mode) in THI mode imaging (the PI method) described above.

FIG. 16 exemplifies four pieces of learning data with learning data IDs of ID1 to ID4. As input data of learning data ID1, a fundamental wave image B1-1 in the positive pulse mode in first THI imaging and the positive pulse mode that is the transmission waveform mode at that time are used. In addition, a THI image obtained as a result of the first THI imaging is used as ground truth data of learning data ID1. As input data of learning data ID2, a fundamental wave image B1-2 in the negative pulse mode in the first THI imaging and the negative pulse mode that is the transmission waveform mode at that time are used. In addition, a THI image obtained as a result of the first THI imaging is used as ground truth data of learning data ID2.

In a similar manner, input data of learning data ID3 is a fundamental wave image B2-1 in the positive pulse mode in second THI imaging and the positive pulse mode, and ground truth data of learning data ID3 is a THI image obtained as a result of the second THI imaging. Input data of learning data ID4 is a fundamental wave image B2-2 in the negative pulse mode in the second THI imaging and the negative pulse mode, and ground truth data of learning data ID4 is a THI image obtained as a result of the second THI imaging.

Performing learning using learning data acquired under various conditions enables learning to be performed with respect to input of various patterns, and an image with favorable image quality can be expected to be estimated in a stable manner even during actual use. Therefore, learning data is favorably obtained by performing THI imaging under different conditions with respect to a same object. It should be noted that, as an object, any of a digital phantom that can be imaged by a transmission/reception simulation of ultrasonic waves, an actual phantom, and an actual living organism may be used.

In addition, preprocessing of learning data may be performed. For example, learning efficiency may be improved by correcting non-uniformity of brightness values due to attenuation of ultrasonic waves. In addition, a harmonic component that is created during a process of an ultrasonic wave propagating inside an object increases as the propagation distance increases. On the other hand, since the harmonic component has a higher frequency than a fundamental wave component, the harmonic component is more affected by attenuation during propagation. In other words, a depth at which harmonic components are accumulated where an effect of THI imaging is produced and a depth at which SN of harmonic components is sufficiently obtained are limited to a certain range. Therefore, preprocessing may be performed by extracting only images at depths in the range described above from THI images and fundamental wave images obtained by THI imaging. Accordingly, a THI image can be estimated from a fundamental wave image even in shallow parts where the effect of THI imaging is small and deep parts where penetration is insufficient and an advantageous effect of improved resolution and contrast is obtained.

Figure 17:
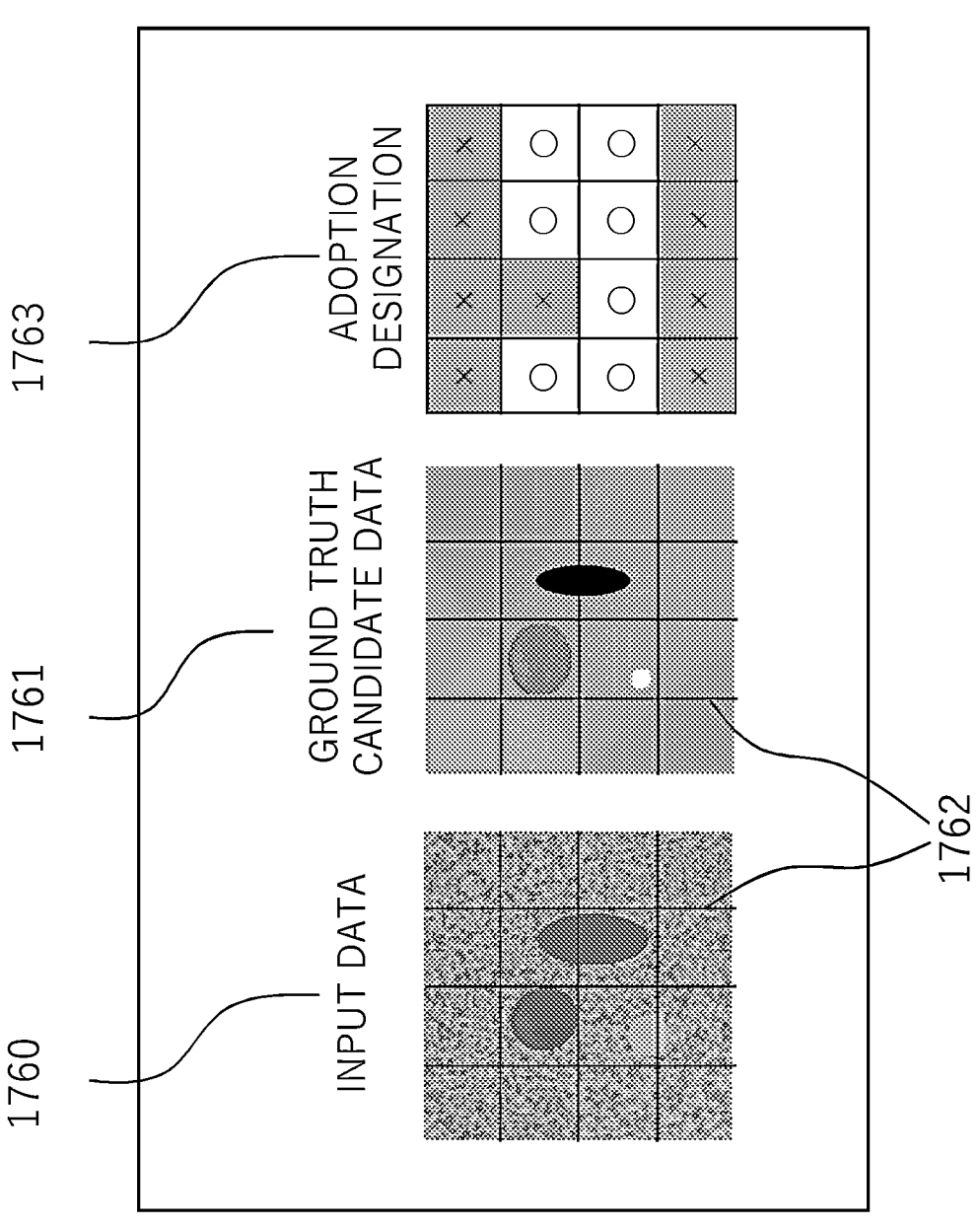
FIG. 17 is a diagram showing an example of a GUI for creating learning data.

In learning, preprocessing of input data and ground truth data may be performed using a GUI such as that shown in FIG. 17. Input data 1760 and ground truth candidate data 1761 are shown in a display screen, and indicators 1762 that divide each piece of data into a plurality of regions are displayed. In the example shown in FIG. 17, images are divided into 16 regions in a 4 by 4 arrangement. An adoption designation box 1763 is a user interface that enables a user to designate whether to adopt or reject each region. The user enters "o" into a region to be adopted as learning data and "x" into a region to be excluded while comparing the input data 1760 and the ground truth candidate data 1761 with each other. Accordingly, locations where unexpected image deterioration has occurred in the ground truth candidate data 1761 and the like can be excluded. For example, shallow parts where the effect of THI imaging is determined to be small and deep parts where penetration is insufficient as described earlier can be excluded. In addition, a location where it is determined that cancellation of the fundamental wave component is insufficient and image quality has declined due to movement of an object while an ultrasonic pulse had been transmitted and received a plurality of times can also be excluded. While FIG. 16 has been described on the assumption that an entire image is to be used as one piece of image data, when an image is divided into a plurality of regions as shown in FIG. 17, an image (a partial image) of each of the regions is used as one piece of learning data. In this case, the learning model accepts an image of a same size (resolution) as the input data 1760 as input and outputs an image of a same size as the ground truth candidate data 1761. In the example shown in FIG. 17, since there are seven regions to be adopted, seven sets of learning data are to be generated.

While a fundamental wave image in THI imaging is used as input data of learning data in the present embodiment, alternatively, a normal B-mode image may be used as input data. In this case, a normal B-mode image refers to a fundamental wave image obtained by transmitting an ultrasonic wave with a central frequency of the ultrasonic probe 102. Accordingly, the learning model can estimate a THI image from a normal B-mode image.

In addition, while a fundamental wave image and a transmission waveform mode are exemplified as input data in the present embodiment, the advantageous effect is produced even when only a fundamental wave image is used as input data. Furthermore, using a transmission frequency and a band of a bandpass filter when acquiring a fundamental wave image as input data enables an estimation to be accurately performed in accordance with a state of the input data. In addition, by further considering information describing which portion of a living organism the object represents, which orientation the ultrasonic probe is in contact relative to a body axis, and the like as input data, learning in accordance with a feature of each site can be performed and estimation accuracy is improved. Examples of a feature of each site include the presence of a surface fat layer, the presence of a high brightness region created by a fascial structure, and the presence of a low brightness region due to a thick blood vessel. Furthermore, by adding information such as a field of medicine, gender, BMI, age, and pathological condition to input data, a learning model corresponding to the feature of each site described earlier in greater detail can be obtained and a further increase in estimation accuracy is expected.

In addition, the learned model 425 of the estimation calculating block 205 mounted to the ultrasonic diagnostic apparatus 1 may be a model having learned image data of all fields of medicine or a model having learned image data of each field of medicine. When a model having learned image data of each field of medicine is mounted, the system control block 109 may cause the user of the ultrasonic diagnostic apparatus 1 to input or select information regarding a field of medicine to change the learned model to be used in accordance with the field of medicine. It is expected that estimation accuracy will further increase by selectively using a model for each field of medicine in which imaging sites are limited to a certain degree.

The learned model 425 obtained by performing learning using a variety of such imaging conditions and a fundamental wave image as input data and a THI image as ground truth data operates on the estimation calculating block 205. As a result, it is expected that the estimation calculating block 205 will estimate and output an image corresponding to a THI image with high resolution or contrast with respect to the input fundamental wave image.

Image Generation Method

Next, details of processing for image generation according to the present embodiment will be described with reference to FIG. 1. When an imaging instruction is input from the user using a GUI (not illustrated), the system control block 109 having received the instruction from the GUI inputs a transmission instruction of ultrasonic waves to the transmission electrical circuit 104. The transmission instruction favorably includes a parameter for calculating a delay time and sound velocity information. Based on the transmission instruction from the system control block 109, the transmission electrical circuit 104 outputs a plurality of pulse signals (voltage waveforms) to the plurality of transducers 101 of the ultrasonic probe 102 through the probe connecting unit 103. In this case, an ultrasonic wave having a fundamental wave component f1 such as that shown in FIG. 14A is adopted as a transmission waveform in the positive pulse mode.

The transmission ultrasonic waves having been transmitted from the plurality of transducers 101 propagate inside the object and create a reflected ultrasonic wave that reflects a difference in acoustic impedances inside the object. The reflected ultrasonic wave is received by the plurality of transducers 101 and converted into a voltage waveform (a voltage signal). The voltage waveform is input to the reception electrical circuit 105 through the probe connecting unit 103. The reception electrical circuit 105 amplifies and digitally samples the voltage waveform as necessary and outputs the voltage waveform as a received signal to the received signal processing block 106. In the received signal processing block 106, with respect to a received signal obtained by the reception electrical circuit 105, the phasing addition processing block 201 performs phasing addition based on an element arrangement and various conditions (aperture control, signal filtering) of image generation that are input from the system control block 109. Furthermore, the signal subjected to phasing addition is saved in the signal storage block 202. Accordingly, received data corresponding to the transmission waveform in the positive pulse mode is saved in the signal storage block 202. By performing similar processing, received data corresponding to a frequency spectrum (a transmission waveform in the negative pulse mode) of which a phase has been inverted with respect to the transmission waveform in the positive pulse mode such as that shown in FIG. 14B is saved in the signal storage block 202.

The calculation processing block 203 cancels a fundamental wave component and extracts a harmonic component using the PI method from a plurality of pieces of received data corresponding to the transmission waveforms in the positive pulse mode and the negative pulse mode and generates harmonic images in which the harmonic component has been enhanced. The images are transmitted to the B-mode processing block 204. The B-mode processing block 204 performs envelope detection processing, logarithmic compression processing, and the like and generates THI image data (harmonic image data) in which signal strength at each point inside the observation region is expressed by brightness intensity.

In addition, the B-mode processing block 204 also performs envelope detection processing, logarithmic compression processing, and the like with respect to the received data in the positive pulse mode and the received data in the negative pulse mode. First and second pieces of fundamental wave image data are generated from the pieces of received data in the positive pulse mode and the negative pulse mode.

The estimation calculating block 205 executes estimation calculation using, as input, the first and second pieces of fundamental wave image data from the B-mode processing block 204, imaging conditions (such as a transmission waveform mode to be input) related to a fundamental wave from the system control block 209, and the like and outputs image data. Using the learned model described earlier, the estimation calculating block 205 estimates first pseudo-THI image data from the first fundamental wave image data and estimates second pseudo-THI image data from the second fundamental wave image data.

In this manner, the estimation calculating block 205 inputs a plurality of pieces of fundamental wave image data obtained from received data used to generate a normal THI image (a harmonic image) to the learned model and estimates a plurality of pseudo-THI images (estimated images) that are equivalent to the normal THI image. It should be noted that, while a pseudo-THI image is estimated from each piece of fundamental wave image data, a pseudo-THI image may be estimated from only a part of the pieces of funda-
mental wave image data. The pieces of received data in the
positive pulse mode and the negative pulse mode in the
image generation processing respectively correspond to "a
received signal that is obtained by transmission/reception of
an ultrasonic wave with one transmission waveform"
according to the present invention. In addition, in the present
embodiment, the first and second pieces of fundamental
wave image data respectively correspond to "third data".
Furthermore, the first and second pseudo-THI images that
are estimated from the first and second pieces of fundamen-
tal wave image data respectively correspond to data that is
estimated by the estimation calculating unit.

The THI image data and the first and second pieces of
pseudo-THI image data are input to the image processing
block 107 and, after being subjected to brightness adjust-
ment, interpolation, and other filtering, the pieces of data are
displayed by the display apparatus 108 according to an
instruction by the system control block 109. Consecutively
displaying the three pieces of image data enables display at
image quality equivalent to THI to be realized at a higher
frame rate than in a normal THI mode.

In addition, when it is determined that image quality of a
normal THI image is low, only the first and second pieces of
pseudo-THI image data may be displayed without display-
ing normal THI image data. When there is a movement of
the object while the first piece of received data and the
second pieces of received data are being obtained, cancel-
lation of the fundamental wave component by the PI method
is not sufficiently performed and image quality of the normal
THI image data declines. In such a case, by displaying only
the first and second pieces of pseudo-THI image data, a
higher frame rate than in a normal THI mode can be realized
while preventing a decline in image quality. Such display is
desirably used when imaging a site in which a movement of
an object is large or the like.

The ultrasonic diagnostic apparatus 1 has a plurality of
display modes in which at least any of an on/off setting of
display of normal THI image data and an on/off setting of
display of pseudo-THI image data differ from one another.
For example, the ultrasonic diagnostic apparatus 1 has a first
mode in which normal THI image data and pseudo-THI
image data are displayed and a second mode in which only
the pseudo-THI image data is displayed. The display modes
may include a third mode in which the pseudo-THI image
data is not displayed and only the normal THI image data is
displayed. Display control of an image based on the display
mode is performed by the system control block 109.

For example, a display mode can be designated by the
user using a GUI (input means) of the display apparatus 108
or determined by the image processing block 107. For
example, the display apparatus 108 may be caused to display
a GUI that enables the user to individually designate on/off
settings of display of a normal THI image and a pseudo-THI
image and accept the user's designation of on/off settings of
display of a normal THI image and a pseudo-THI image via
the GUI.

A determination of mode selection may be made by the
image processing block 107 or the system control block 109.
For example, the image processing block 107 may deter-
mine whether or not image quality of a normal THI image
is higher than a threshold and select a display mode based on
a determination result. Specifically, when the image quality
of a normal THI image is higher than the threshold, the mode
for displaying both a normal THI image and a pseudo-THI
image is selected, but when the image quality is lower than
the threshold, the mode for displaying a pseudo-THI image without displaying a normal THI image is selected. The
image quality of a normal THI image can be determined
based on an amount of movement of an object. For example,
the image processing block 107 may determine whether or
not image quality of a normal THI image is higher than a
threshold according to whether or not a movement of an
object that is obtained based on first and second pieces of
fundamental wave image data or first and second pieces of
pseudo-THI image data is at least a prescribed amount.
Alternatively, the image processing block 107 may deter-
mine the image quality of a normal THI image based on
whether or not a fundamental wave component included in
a signal obtained by adding up the first and second pieces of
received data is at least a prescribed amount.

FIGS. 18A to 18D schematically show a display example
of an image on the display apparatus 108. A display screen
1800 includes an image display region 1801, a frame rate
display region 1802, an indicator 1803 indicating whether
display of a normal THI image is on/off, and an indicator
1804 indicating whether display of a pseudo-THI image is
on/off. The indicators 1803 and 1804 may double as buttons
(GUIs) for switching display of a normal THI image and a
pseudo-THI image on or off.

Figures 18A, 18B, 18C, 18D:
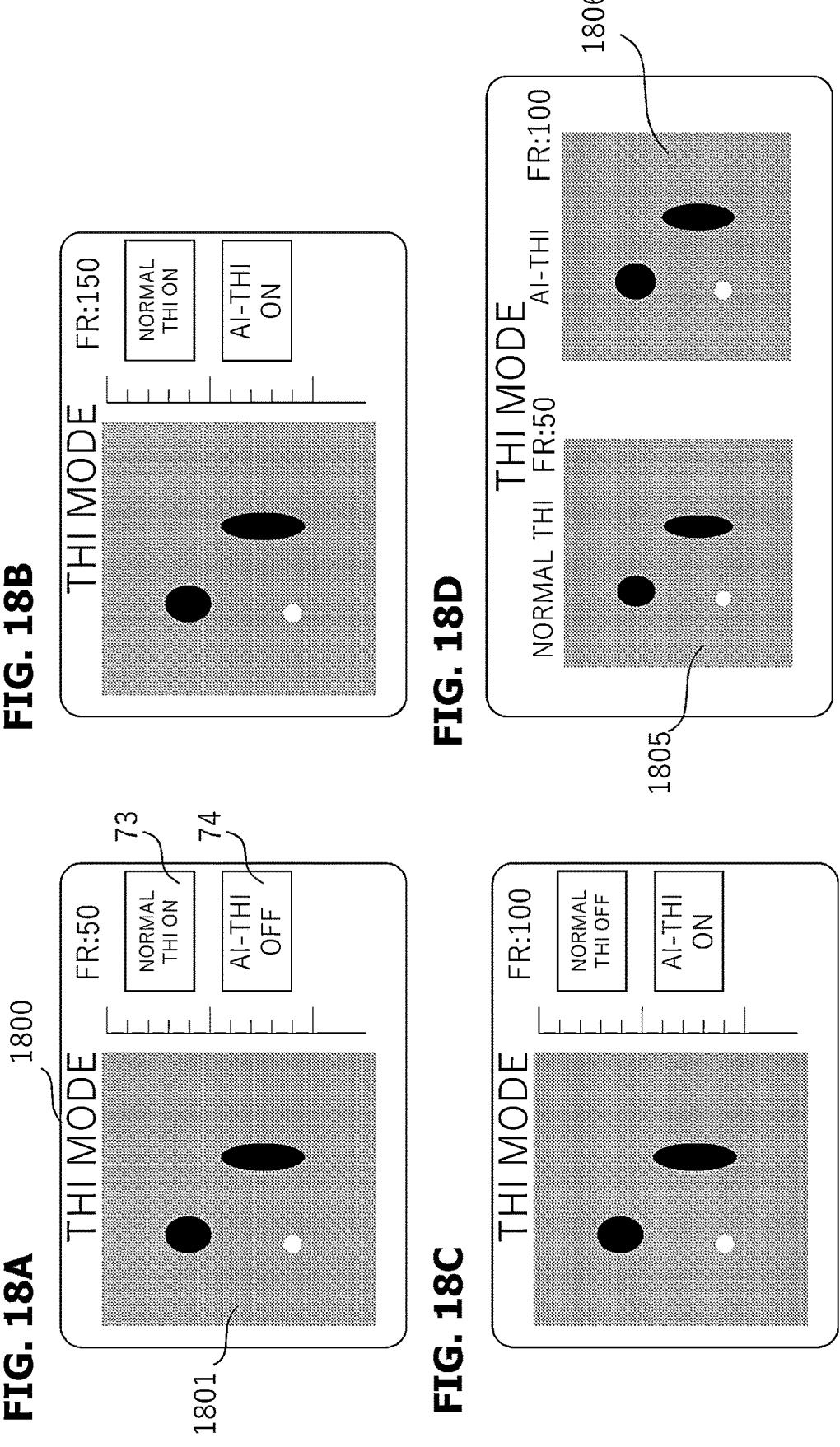
FIGS. 18A to 18D are diagrams showing an example of display of an ultrasonic image by a display apparatus.

FIG. 18A shows a display example of display in the
normal THI mode or, in other words, a mode for displaying
a normal THI image and not displaying a pseudo-THI image
(an AI-THI image). A frame rate (FR) is set to 50 fps. Since
a normal THI image is being displayed, the indicator 1803
displays "Normal THI: ON", and since a pseudo-THI image
is not displayed, the indicator 1804 displays "AI-THI: OFF".

FIG. 18B shows a display example in a mode in which
both a normal THI image and a pseudo-THI image are
displayed. In this display mode, the normal THI image and
the pseudo-THI image are consecutively displayed in the
image display region 1801. Since pseudo-THI image data
can be estimated from each of fundamental wave images
based on the first and second pieces of received data, in the
present mode, the frame rate increases threefold to 150 fps
as compared to FIG. 18A. In the present embodiment, the
indicator 1804 displays "AI-THI: ON". Accordingly, the fact
that an estimated image having been estimated by the
estimation calculating block 205 is included in a display
image can be clearly indicated to the user. While the
indicator 1804 in the present embodiment notifies that an
estimated image is to be displayed by character display,
display of the estimated image may be notified by other
systems. For example, methods such as changing a color of
an outer edge of a display image or a display region, causing
the outer edge to blink, and changing a color, chroma, or a
pattern of a background of the display image or the display
region may be adopted.

FIG. 18C shows a display example in a mode for dis-
playing a pseudo-THI image and not displaying a normal
THI image. The frame rate in the present mode is 100 fps
which is double the frame rate in FIG. 18A. The indicator
1803 displays that display of a normal THI image is off
(Normal THI: OFF) and the indicator 1804 displays that
display of a pseudo-THI image is on "AI-THI: ON".

FIG. 18D is an example in which a normal THI image
1805 and a pseudo-THI image 1806 are displayed side by
side. Only the normal THI image is displayed on a left side
of a screen at a frame rate of 50 fps, and only the pseudo-THI
image is displayed on a right side of the screen at a frame
rate of 100 fps. Using the display screen enables the user to
not only confirm the estimated image but also simultane-
ously confirm the normal THI image that is a ground truth image. Such a display screen is useful when evaluating or checking accuracy and reliability of the estimation calculating block 205.

Fourth Embodiment

Next, another embodiment of the present invention will be described. In the third embodiment, a fundamental wave image obtained in the THI mode is input to the estimation calculating block 205 to estimate a pseudo-THI image. In the present embodiment, image data having been imaged in a normal B-mode is input to the estimation calculating block 205 to estimate a pseudo-THI image. Even in the present embodiment, an image with image quality that is equivalent to THI can be obtained without causing a drop in a frame rate by the PI method.

An overall configuration of the ultrasonic diagnostic apparatus 1 is similar to that of the third embodiment (FIG. 1). A flow from transmitting an ultrasonic wave with respect to the object 100 up to inputting a received signal to the received signal processing block 106 is similar to that of the third embodiment. However, while both the fundamental wave component f1 and the harmonic component 2/1 are adjusted so as to be included in an effective frequency band of the ultrasonic probe 102 in the third embodiment, in the present embodiment, the harmonic component 2/1 may be outside of the effective frequency band of the ultrasonic probe 102. In other words, in the present embodiment, a transmission waveform having a bandwidth at which the fundamental wave component f1 matches the effective frequency band of the ultrasonic probe 102 can be used. Furthermore, a transmission waveform may be used in which the fundamental wave component f1 is included in the effective frequency band of the ultrasonic probe 102 but the harmonic component 2/1 is not included in the effective frequency band of the ultrasonic probe 102 or, in other words, a transmission waveform may be used in which the fundamental wave component f1 has a higher frequency than in the third embodiment.

FIG. 12 is a diagram showing details of a received signal processing block 116 according to the fourth embodiment. The received signal processing block 116 has a phasing addition processing block 201, a signal storage block 202, a B-mode processing block 204, and an estimation calculating block 205. Functions and processing of each block are basically the same as the block with the same name in the third embodiment. In other words, a received signal loaded from the reception electrical circuit 105 is subjected to phasing addition by the phasing addition processing block 201 and saved in the signal storage block 202. Subsequently, the B-mode processing block 204 generates a normal B-mode image and inputs the normal B-mode image to the estimation calculating block 205. The estimation calculating block 205 inputs the normal B-mode image to a learned model and obtains a pseudo-THI image (an estimated image) as an estimation result. In the present embodiment, the estimated image is used for display on the display apparatus 108.

According to the present embodiment, a pseudo-THI image can be acquired even when the ultrasonic probe 102 is unable to receive the harmonic component 2/1. In other words, a frequency of a transmission ultrasonic wave need not be lowered in order to receive a harmonic component. Since the higher the frequency of an ultrasonic wave, the higher the resolution of an obtained image, according to the present embodiment, estimation accuracy of a pseudo-THI image in the estimation calculating block 205 also improves.

A learned model included in the estimation calculating block 205 according to the present embodiment is generated by processing similar to that performed in the third embodiment. In the present embodiment, a normal B-mode image obtained by transmitting/receiving an ultrasonic wave with a central frequency of the ultrasonic probe 102 may be used as input data that is included in learning data. However, a learned model having been learned based on the same learning data as the third embodiment may also be used.

OTHER EMBODIMENTS

The embodiments described above merely represent specific examples of the present invention. A scope of the present invention is not limited to the configurations of the embodiments described above and various embodiments can be adopted without departing from the spirit of the invention.

For example, while a model using a B-mode image as input data and an estimated image as output data has been used in the first and second embodiments, an input and an output of a model need not be images. For example, received data obtained by normal B-mode imaging may be used as-is as input data or received data after being subjected to phasing addition processing may be used as input data. In such cases, as ground truth data, received data subjected to compound processing may be used as-is or received data after being subjected to phasing addition processing and compound processing may be used. A similar operational effect to the embodiments described above can be produced even when using such models.

In addition, for example, while a learning model using a B-mode image as input data and an estimated image as output data has been used in the third and fourth embodiments, model input/output need not be images and need only be data to be a source of image generation. For example, received data obtained by fundamental wave transmission may be used as-is as input data or received data after being subjected to phasing addition processing may be used as input data. In such cases, as ground truth data, received data obtained by only extracting a harmonic component may be used as-is or received data obtained by only extracting a harmonic component and then being subjected to phasing addition processing may be used. A similar operational effect to the embodiments described above can be produced even when using such models. It should be noted that, when an output of a model is not an image, the received signal processing block 106 may further include an image generating unit that generates an image based on data that is output from the estimation calculating block 205. The image generating unit is configured to generate an estimated image that is equivalent to a harmonic image from data having been estimated by the estimation calculating block 205 (the estimation calculating unit).

Furthermore, the disclosed technique can take the form of an embodiment of, for example, a system, an apparatus, a method, a program, or a recording medium (a storage medium). Specifically, the disclosed technique may be applied to a system constituted by a plurality of devices (for example, a host computer, an interface device, an imaging apparatus, and a web application) or to an apparatus constituted by a single device.

It is needless to say that the object of the present invention can be realized by performing the following. A recording medium (or a storage medium) on which is recorded a program code (a computer program) of software that realizes functions of the embodiments described above is supplied to a system or an apparatus. It is needless to say that the storage medium is a computer-readable storage medium. In addition, a computer (or a CPU or an MPU) of the system or the apparatus reads and executes the program code stored in the recording medium. In this case, the program code itself having been read from the recording medium is to realize the functions of the embodiments described above and the recording medium on which the program code is recorded is to constitute the present invention.

One aspect of the disclosure is an ultrasonic diagnostic apparatus, comprising: an ultrasonic probe which scans an observation region in an object with an ultrasonic wave; and an estimated image generating unit which uses a model having been machine-learned using learning data including first data based on a first received signal that is obtained by one scan of an ultrasonic wave and second data based on a second received signal that is obtained by a plurality of scans, in which a transmission direction or a central frequency of an ultrasonic wave has been changed, to generate an estimated image equivalent to image data obtained by a plurality of scans, in which a transmission direction or a central frequency of an ultrasonic wave has been changed, from third data based on a third received signal that is obtained by one scan of an ultrasonic wave by the ultrasonic probe.

Another aspect of the disclosure is an ultrasonic diagnostic apparatus, comprising: an ultrasonic probe which scans an observation region in an object with an ultrasonic wave; and an estimated image generating unit which uses a model having been machine-learned using learning data including first data based on a first received signal obtained by transmission/reception of an ultrasonic wave with one transmission waveform and second data based on a second received signal that is obtained by transmission/reception of ultrasonic waves with a plurality of different transmission waveforms, to generate an estimated image equivalent to image data obtained by transmission/reception of ultrasonic waves with a plurality of different transmission waveforms from third data based on the third received signal obtained by transmission/reception equivalent to transmission/reception of an ultrasonic wave with one transmission waveform by the ultrasonic probe.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An ultrasonic diagnostic apparatus, comprising:
an ultrasonic probe which scans an observation region in an object with an ultrasonic wave;
at least one memory storing a program; and
at least one processor, which, by executing a program, causes the ultrasonic apparatus to:
generate an enhanced image by inputting first data into a learned model, wherein the first data is obtained by a transmission/reception of an ultrasonic wave from the ultrasonic probe to the object in a first mode,
wherein the learned model is a model trained using machine learning with second data obtained by executing the first mode and third data generated by combining a plurality of received signals obtained by executing a second mode, wherein the second mode is a mode that generates a harmonic image by reducing a fundamental frequency component based on multiple signals obtained by performing multiple transmission/receptions of ultrasonic waves with different waveforms,
wherein the third data is the harmonic image generated by the second mode, and
wherein the enhanced image is a pseudo-harmonic image corresponding to the harmonic image.

2. The ultrasonic diagnostic apparatus according to claim 1,
wherein the at least one processor causes the ultrasonic diagnostic apparatus to display, on a display unit, the enhanced image with an indicator indicating that the enhanced image is being displayed.

3. The ultrasonic diagnostic apparatus according to claim 1,
wherein the at least one processor causes the ultrasonic diagnostic apparatus to display, on a display unit at least one of an ultrasonic image generated without using the learned model based on data obtained by performing the second mode on the object, and the enhanced mode, with an indicator indicating the enhanced mode is being displayed.

4. The ultrasonic diagnostic apparatus according to claim 1, wherein the multiple transmission/receptions of ultrasonic waves with different waveforms in the second mode are multiple transmissions/receptions of ultrasonic waves with different phases.

5. The ultrasonic diagnostic apparatus according to claim 1,
wherein multiple instances of the first data are obtained by performing the first mode multiple times on the object, and multiple enhanced images are generated by inputting the multiple instances of the first data into the learned model.

6. The ultrasonic diagnostic apparatus according to claim 1, wherein the first mode is a mode that generates a B-mode image by transmitting and receiving ultrasonic waves without changing transmission direction and the central frequency.

7. An ultrasonic diagnostic method comprising a step of:
generating an enhanced image by inputting first data into a learned model,
wherein the first data is obtained by a transmission/reception of an ultrasonic wave from an ultrasonic probe to an object in a first mode,
wherein the learned model is a model trained using machine learning with second data obtained by executing the first mode and third data generated by combining a plurality of received signals obtained by executing a second mode,
wherein the second mode is a mode that generates a harmonic image by reducing a fundamental frequency component based on multiple signals obtained by performing multiple transmission/receptions of ultrasonic waves with different waveforms,
wherein the third data is the harmonic image generated by the second mode, and
wherein the enhanced image is a pseudo-harmonic image corresponding to the harmonic image.

8. A computer-readable storage medium non-transitorily storing a program causing a processor, when executed by the processor, to:
generate an enhanced image by inputting first data into a learned model,
wherein the first data is obtained by a transmission/reception of an ultrasonic wave from an ultrasonic probe to an object in a first mode,
wherein the learned model is a model trained using machine learning with second data obtained by executing the first mode and third data generated by combining in a plurality of received signals obtained by executing a second mode, wherein the second mode is a mode that generates a harmonic image by reducing a fundamental frequency component based on multiple signals obtained by performing multiple transmission/receptions of ultrasonic waves with different waveforms,
wherein the third data is the harmonic image generated by the second mode, and
wherein the enhanced image is a pseudo-harmonic image corresponding to the harmonic image.

9. An information processing apparatus, comprising:
at least one memory storing a program; and
at least one processor which, by executing the program, causes the information processing apparatus to:
generate an enhanced image by inputting first data into a learned model, wherein the first data is obtained by a transmission/reception of an ultrasonic wave from an ultrasonic probe to an object in a first mode,
wherein the learned model is a model trained using machine learning with second data based on a second data obtained by executing the first mode and third data generated by combining a plurality of received signals obtained by executing a second mode, wherein the second mode is a mode that generates a harmonic image by reducing a fundamental frequency component based on multiple signals obtained by performing multiple transmission/receptions of ultrasonic waves with different waveforms,
wherein the third data is the harmonic image generated by the second mode, and
wherein the enhanced image is a pseudo-harmonic image corresponding to the harmonic image.

* * * * *